(12) United States Patent
Krivts et al.

(10) Patent No.: US 10,687,735 B2
(45) Date of Patent: Jun. 23, 2020

(54) DEVICE AND METHOD FOR ESTIMATION OF PULMONARY FUNCTION CHARACTERISTICS

(71) Applicant: TECHNOPULM LTD., Rehovot (IL)

(72) Inventors: Igor Krivts, Rehovot (IL); Yuri Belenky, Be'er Ya'akov (IL)

(73) Assignee: TECHNOPULM LTD., Rehovot (IL)

( * ) Notice: Subject to any disclaimer, the term of this patent is extended or adjusted under 35 U.S.C. 154(b) by 0 days.

(21) Appl. No.: 16/485,646

(22) PCT Filed: Mar. 5, 2018

(86) PCT No.: PCT/IL2018/050245
§ 371 (c)(1),
(2) Date: Aug. 13, 2019

(87) PCT Pub. No.: WO2018/163160
PCT Pub. Date: Sep. 13, 2018

(65) Prior Publication Data
US 2020/0046255 A1    Feb. 13, 2020

(30) Foreign Application Priority Data
Mar. 6, 2017    (IL) .......................................... 250970

(51) Int. Cl.
*A61B 5/085*    (2006.01)
*A61B 5/091*    (2006.01)
*A61B 5/087*    (2006.01)
*A61B 5/09*    (2006.01)
*A61B 5/097*    (2006.01)

(52) U.S. Cl.
CPC ............ *A61B 5/085* (2013.01); *A61B 5/0871* (2013.01); *A61B 5/0876* (2013.01); *A61B 5/09* (2013.01); *A61B 5/091* (2013.01); *A61B 5/097* (2013.01)

(58) Field of Classification Search
CPC ..... A61B 5/085; A61B 5/0871; A61B 5/0876; A61B 5/09; A61B 5/091; A61B 5/097
See application file for complete search history.

(56) References Cited

U.S. PATENT DOCUMENTS

| | | |
|---|---|---|
| 3,511,237 A | 5/1970 | Jaeger |
| 4,182,172 A | 1/1980 | Wennberg et al. |
| 4,220,161 A | 9/1980 | Berlin et al. |
| 4,324,260 A | 4/1982 | Puderbaugh |
| 4,638,812 A | 1/1987 | Haekkinen |

(Continued)

FOREIGN PATENT DOCUMENTS

| | | |
|---|---|---|
| FR | 2659413 A1 | 9/1991 |
| WO | 2016185470 A1 | 11/2016 |

OTHER PUBLICATIONS

McKenzie et al., (2002) Airway resistance measured by the interrupter technique: normative data for 2-10 year olds of three ethnicities. Arch Dis Child 87(3): 248-251.

(Continued)

*Primary Examiner* — Meredith Weare
(74) *Attorney, Agent, or Firm* — The Roy Gross Law Firm, LLC; Roy Gross

(57) ABSTRACT

The present invention relates to the field of medical devices, and, more particularly, to a portable system for testing one or more lung functions, and novel techniques for noninvasive determination of one or more pulmonary function characteristics.

27 Claims, 12 Drawing Sheets

(56) References Cited

U.S. PATENT DOCUMENTS

| | | | |
|---|---|---|---|
| 4,944,306 | A | 7/1990 | Alvino |
| 5,233,998 | A | 8/1993 | Chowienczyk et al. |
| 5,634,471 | A | 6/1997 | Fairfax et al. |
| 5,680,871 | A | 10/1997 | Ganshorn |
| 5,984,872 | A | 11/1999 | Vriend |
| 6,068,602 | A | 5/2000 | Tham et al. |
| 6,068,606 | A | 5/2000 | Castel et al. |
| 7,094,208 | B2 | 8/2006 | Williams et al. |
| 7,383,740 | B2 | 6/2008 | Krasilchikov et al. |
| 8,657,757 | B2 | 2/2014 | Lazar et al. |
| 2011/0201958 | A1 | 8/2011 | Lazar et al. |
| 2013/0190640 | A1 | 7/2013 | Adam et al. |
| 2015/0057559 | A1 | 2/2015 | Palti |
| 2016/0038057 | A1 | 2/2016 | Johnson et al. |
| 2016/0256073 | A1 | 9/2016 | Grudin et al. |
| 2018/0168484 | A1* | 6/2018 | Rahamim .............. A61B 5/085 |
| 2019/0246953 | A1* | 8/2019 | Lazar, Jr. .............. A61B 5/091 |

OTHER PUBLICATIONS

Nikischin et al., (1998) A new method to analyze lung compliance when pressure-volume relationship is nonlinear. Am J Respir Crit Care Med 158(4): 1052-1060.
International Search Report PCT/IL2018/050245 completed Jun. 25, 2018; dated Jun. 26, 2018 3 pages.
Written Opinion of the International Searching Authority PCT/IL2018/050245 dated Jun. 26, 2018 4 pages.

* cited by examiner

DEVICE AND METHOD FOR ESTIMATION OF PULMONARY FUNCTION CHARACTERISTICS

RELATED APPLICATIONS

This application is a National Phase of PCT Patent Application No. PCT/IL2018/050245 having International filing date of Mar. 5, 2018, which claims the benefit of priority of Israeli Patent Application No. 250970 filed on Mar. 6, 2017. The contents of the above applications are all incorporated by reference as if fully set forth herein in their entirety.

FIELD OF THE INVENTION

The present invention relates to the field of medical devices, and, more particularly, to a portable system for testing lung functions, and to methods for noninvasive determination of one or more pulmonary function characteristics.

BACKGROUND OF THE INVENTION

The performance of the respiratory system is generally examined by pulmonary function tests (PFT), which are a broad range of tests that are usually done in a health care provider's office and at specialized facilities. The PFT characteristics are considered important and informative data for the respiration of a patient. However, its measurement has not yet been implemented in routine clinical practice because of the rather complicated apparatus required.

There are major categories of respiratory characteristics that may be obtained with pulmonary functional tests: 1) spirometric characteristics, 2) lung volumetric parameters, 3) airway resistance and 4) lung compliance.

Spirometric Characteristics.

In a spirometry test, a person breathes into a mouthpiece that is connected to a device called a spirometer. New generation spirometers are handheld, small, lightweight and fit into a general practitioner's office. Spirometers are either a volumetric type which measure the amount of air exhaled or inhaled within a certain time, as described, for example, in U.S. Pat. Nos. 4,944,306 and 4,324,260, or a flow type which measure how fast the air flows in or out from lungs, as described, for example, in U.S. Pat. Nos. 4,182,172; 4,638,812; 7,094,208 and 7,383,740.

Lung Volumetric Parameters.

Plethysmography is considered the "gold standard" for measuring lung volumes. A patient is situated in plethysmographs, also known as "body boxes" having a known volume and pants against a closed shutter to produce changes in the box pressure. Such devices are disclosed, for example, in U.S. Pat. Nos. 3,511,237 and 5,680,871. In addition to lung volume measurements, plethysmography allows estimating airway resistance, spirometry performance, and dynamic lung compliance (using a special subsystem). The main disadvantages of this equipment are high price, bulkiness, and difficulties with measurements in children, claustrophobic, and bed ridden patients, which cause inconvenience and limited accessibility.

U.S. Pat. No. 8,657,757 and U.S. Patent Application 2013/0190640, disclose devices and methods for measuring volumetric parameters, spirometric parameters, and lung compliance by deriving pulmonary volumes from flow rates without using a "body box". The method includes measurement of a plurality of airflow rates and pressures within a chamber during interruptions of forced exhalation.

Airway Resistance.

The airway resistance refers to resistance in the respiratory tract to airflow. The airway resistance is defined as the ratio of driving pressure to the rate of air flow and is measured under dynamic conditions (when air is flowing). The resistance can change based on the health and conditions of the lungs. Most lung diseases increase airway resistance in many different ways. For example, in asthma attacks the bronchioles spasm increases resistance; emphysema also increases airway resistance because the lung tissue becomes too pliable; many lung infections increase a mucus production that also increasing the airway resistance. The airway resistance may be estimated by plethysmography that is considered as "gold standard". Additional methods for airway resistance estimation are disclosed in U.S. Pat. Nos. 4,220,161; 5,233,998; 6,068,606 and U.S. Patent Application 2015/0057559.

Lung Compliance.

Lung compliance is defined as the volume change per unit of pressure change across the lung, and is an important indicator of lung health and function. Measurements of lung volumes differ at the same pressure between inhalation and exhalation, meaning that lung compliance differs between inhalation and exhalation.

Low compliance indicates stiff lungs and means extra work is required to bring in a normal volume of air. Disease states resulting in low compliance include the Adult Respiratory Distress Syndrome (ARDS), pulmonary edema, pneumonectomy, pleural effusion, pulmonary fibrosis, and pneumonia among others. Emphysema is a typical cause of increased lung compliance. Lung compliance varies with the size of the lungs; a child has a smaller compliance than an adult does.

The lung compliance may be estimated by the formula detailed in Nikischin et al. (1998), Am. J. Respir. Crit. Med., Vol. 158, pp. 1052-1060.

Additional methods for lung compliance estimation are disclosed in U.S. Pat. No. 6,068,602 and U.S. Patent Application 2016/0256073.

Diagnosis of Lung Diseases.

The main clinical roles of respiratory function tests include diagnosis, assessment of severity, monitoring treatment and evaluation of prognosis.

Spirometry is one the most useful diagnostic tests, which measures vital capacity and force expiratory volume in 1 second. These parameters permit differentiation between restrictive and obstructive respiratory diseases. The spirogram flow-volume curves are used for diagnosis, however, combined diseases are not always visible in such graphs as their single elements. Further tests, like diffusion or provocation testing, provide a physician with more information.

U.S. Pat. No. 5,984,872 describes a spirometer with special electronic module, which is electrically connected to a computer through an analogue to digital converter that allows calculating and evaluating an expiratory flow-volume curve shape for diagnostic analyses. U.S. Publication No. 2011/0201958 discloses a hand-held device for determining at least one pulmonary function, designed to minimize measured air displacement due to shuttering. U.S. Pat. No. 5,634,471 discloses a flowmeter for measuring peak expiratory flow. U.S. publication 2016/0038057 discloses an airflow perturbation device for measuring respiratory resistance, compliance, and inertance. International application, Publication No. WO 2016/185470, discloses a pulmonary function testing device for measuring air flow while a subject breathes through two or more air flow resistors, including computational analysis done in order to obtain the subjects' respiratory related parameters.

There is an unmet medical need for a device for pulmonary function tests, which is hand-held, portable, and inexpensive. The device should be sufficiently easy to use for patients themselves to perform home monitoring. It should not require extensive maintenance. The system should also be capable of interfacing with a computer or the internet to allow convenient data collection. In addition, such apparatus should be used under various conditions, including stress, and the like. In addition, it is very important to develop of the simple and effective methods to determination of the basic functional properties of the respiratory system. In addition, the proposed Spiro-Test System (STS) should be owned of acceptable accuracy and reliability, and its measurement process no effect on the natural condition of the lung.

SUMMARY OF THE INVENTION

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other advantages or improvements.

According to some embodiments, there are provided devices, assemblies and methods for estimating one or more pulmonary function characteristics by analysis of pressure signals obtained during forced gas exhalation into a chamber through a gas inlet port, and measured within said chamber, wherein the total effective outlet area through which gas flows to the open atmosphere may be changed during exhalation by displacing a shutter module coupled to the outlet of the chamber, from first end position to second end position, in response to the pressure signal descending below a predetermined threshold after reaching peak pressure value.

The present invention is based, in part, on the unexpected discovery that one or more pulmonary function characteristics is derived primarily from analysis of pressure signals, devoid of direct flow measurements. A great benefit of the analysis is that a single exhalation is sufficient for obtaining the pulmonary function characteristics. Moreover, during the course of exhalation, resistance to flow is modified, but not blocked. This analysis enables to derive parameters with comparable reliability and accuracy to known methods that usually require full body measurement. Advantageously, the devices disclosed herein are compact, operated when handheld and are portable, thus can be produced at low cost. Other advantages of the devices include low cost of usage as they require less power and less maintenance. The aforementioned advantages render the use of the devices most convenient while not compensating on the quality of measurements.

In accordance with some embodiments, there is provided a device for determining at least one pulmonary function characteristic, the device comprising at least one chamber (the chamber comprises at least one gas inlet port configured to receive gas flow, a distal element comprising at least one distal opening and at least one pressure transducer configured to detect pressure within the at least one chamber and to produce a signal upon detecting pressure at about a predetermined threshold), at least one shutter module connected to said distal element, said at least one shutter module comprising at least one shutter opening and a first total effective area positioned within the at least one shutter module or at the vicinity of the at least one shutter module, configured to allow passage of the gas flow therethrough. In accordance with some embodiments, the at least one shutter module is configured to be displaced upon receiving the signal, or a signal derived therefrom, and wherein upon said displacement the first total effective area changes to a second total effective area.

In accordance with some embodiments, the chamber further comprises a laminar flow diffuser.

In accordance with some embodiments, the device further comprises a mouthpiece connected to the at least one gas inlet port, and configured to enable delivery of exhaled gas flow to the at least one gas inlet port.

In accordance with some embodiments, the device further comprises a handle connected to the at least one chamber.

In accordance with some embodiments, the device further comprises an actuator configured to displace, or induce displacement, of the at least one shutter module upon receiving the first signal, or a signal derived from said first signal.

In accordance with some embodiments, the actuator is a rotary actuator and the shutter module is a shutter wheel having a circular form, and wherein the actuator is configured to displace, or to induce displacement of, the at least one shutter wheel by rotation.

In accordance with some embodiments, the device further comprises a shutter pin and a hard stop comprising a groove, wherein the shutter pin is located within the groove, and wherein the shutter pin is configured to limit the range of displacement of the shutter module.

In accordance with some embodiments, the device further comprises a control module, wherein the control module is configured to receive one or more signals from the at least one pressure transducer.

In accordance with some embodiments, the control module is configured to provide the one or more signals to the actuator.

In accordance with some embodiments, the control module is configured to transmit the one or more signals to an external device.

In accordance with some embodiments, the control module is configured to transmit the one or more signals to the external device in real time.

In accordance with some embodiments, the control module is configured to store the one or more signals.

In accordance with some embodiments, the shutter wheel comprises at least one shutter opening, wherein the at least one shutter opening allows passage of gas flow from the at least one distal opening through the area enclosed by the perimeter of the at least one shutter opening, or through any portion thereof.

In accordance with some embodiments, the shutter wheel and said distal element are detached from one another allowing passage of gas flow from the at least one distal opening through an area extending between the circumference of said shutter wheel and said distal element.

In accordance with some embodiments, the shutter wheel comprises at least one shutter edge opening, wherein the at least one shutter edge opening allows passage of gas flow from the at least one distal opening through the area enclosed by the perimeter of the at least one shutter edge opening, or through any portion thereof.

In accordance with some embodiments, the at least one pressure transducer is configured to detect pressure within the space between the laminar flow diffuser and the distal element.

In accordance with some embodiments, there is provided a method for evaluating at least one pulmonary function characteristic in a subject in need thereof, comprising the steps of providing the device as described hereinabove, receiving gas exhalation from a subject in need thereof, through the gas inlet port, detecting pressure within the at least one chamber, producing pressure versus time curve and identifying a first peak pressure, toggling the shutter module if the detected pressure post the first peak pressure is within the range of a predetermined pressure threshold, identifying a second peak pressure and an end point pressure in the pressure versus time curve and deriving from said pressure versus time curve at least one value related to at least one pulmonary function characteristics of said subject in need thereof.

In accordance with some embodiments, the method further comprises the step of identifying on the curve of step (vi) a pressure volume indicator point, wherein the pressure volume indicator point post the second peak pressure is a pressure within the range of a predetermined pressure threshold.

In accordance with some embodiments, the at least one value comprises any one or more of TGV and TLC, and wherein the derivative of said pressure versus time curve includes at least one linear portion.

In accordance with some embodiments, the method further comprises identifying on the curve of step (vi) a pressure volume indicator point, wherein the at least one linear portion is the derivative of the pressure during a time period encompassing the pressure volume indicator point.

In accordance with some embodiments, the at least one value comprises any one or more of TGV and TLC, and wherein said pressure versus time curve includes at least one exponential portion.

In accordance with some embodiments, the at least one exponential portion is during a time period extended between the second peak pressure and the end point pressure.

In accordance with some embodiments, the at least one value comprises any one or more of TGV and TLC, and wherein said pressure versus time curve includes at least one parabolic portion.

In accordance with some embodiments, the at least one parabolic portion is the pressure during a time period extended between the second peak pressure and the end point pressure.

In accordance with some embodiments, the method further comprises the step of determining an airway resistance based on the predetermining pressure threshold and the second peak pressure.

In accordance with some embodiments, the method further comprises the step of determining a lung compliance based on the airway resistance and the end point pressure.

In accordance with some embodiments, the method further comprises determining a group of volume related indices; and producing a diagnostic event based on the group of volume related indices.

BRIEF DESCRIPTION OF THE FIGURES

Some embodiments of the invention are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention. For the sake of clarity, some objects depicted in the figures are not to scale.

In the Figures.

DETAILED DESCRIPTION OF SOME EMBODIMENTS

Figure 1A:
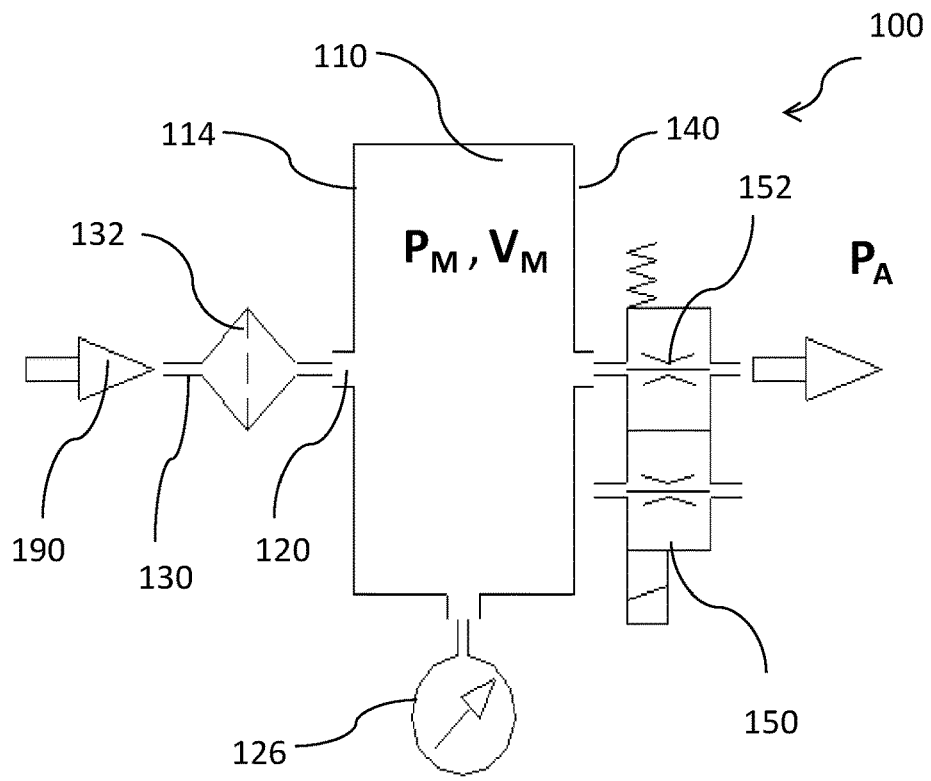
FIG. 1a constitutes a schematic diagram of a pulmonary function test device, in accordance with some embodiments, in a state of a first end position.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure. In the figures, like reference numerals refer to like parts throughout.

As used herein the terms "subject" and "patient" are interchangeable, and refer to the user of the devices and methods disclosed herein and include a healthy user, in the context of the measured values or a subject having, or being susceptible to have, a pulmonary disease or disorder. The subject may be a person or a mammal.

As used herein, the terms "about" or "within the range of" mean in the range of, roughly, or around. In general, the terms "about" or "within the range of" are used to modify a numerical value above and below the stated value by 20%. According to some embodiments, the term "about" or "within the range of" are used to modify a numerical value above and below the stated value by 15% thereof. According to some embodiments, the term "about" or "within the range of" are used to modify a numerical value above and below the stated value by 10% thereof.

Figure 1B:
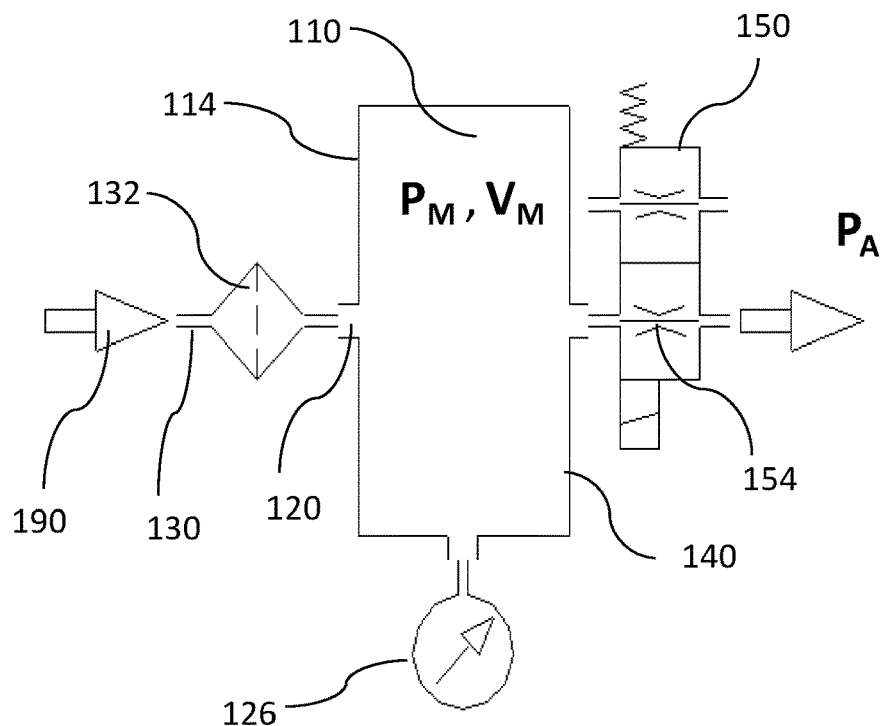
FIG. 1b constitutes a schematic diagram of a pulmonary function test device, in accordance with some embodiments, in a state of a second end position FIG. 2 constitutes a view in perspective of a pulmonary function test device, in accordance with some embodiments.

Reference is now made to FIGS. 1a-1b. FIG. 1a constitutes a schematic diagram of a pulmonary function test device 100 in accordance with some embodiments, in a state of a first end position. FIG. 1b constitutes a schematic diagram of a pulmonary function test device 100 in accordance with some embodiments, in a state of a second end position. The device 100 comprises a main chamber 110 having an absolute pressure $P_M$, and volume $V_M$, a proximal end 114, a distal end 140, a pressure transducer 126 and shutter module 150. The pressure transducer 126 measures the pressure within main chamber 110. A mouthpiece 130 which may include an anti-bacteriological filter 132 is mounted on the gas inlet port 120 located at the proximal end 114 of the main chamber 110, in accordance with some embodiments. Shutter module 150 may either be in a state of first end position (see FIG. 1a) or in a state of second end position (see FIG. 1b). In FIG. 1a, in accordance with some embodiments, exhalation gas flow 190 flows from mouthpiece 130 through chamber 110 then through shutter module 150 to the atmosphere, having atmospheric pressure $P_A$, via shutter opening 152, having a first total effective area $A_{S1}$, when shutter module 150 is in first end position. In FIG. 1b, in accordance with some embodiments, exhalation gas flow 190 flows from mouthpiece 130 through chamber 110 then through shutter module 150 to the atmosphere via shutter opening 154, having a second total effective area $A_{S2}$, when shutter module 150 is in second end position.

The terms "flow", "gas flow", "exhalation gas flow" and "flow rate" as used herein are interchangeable.

Figure 2:
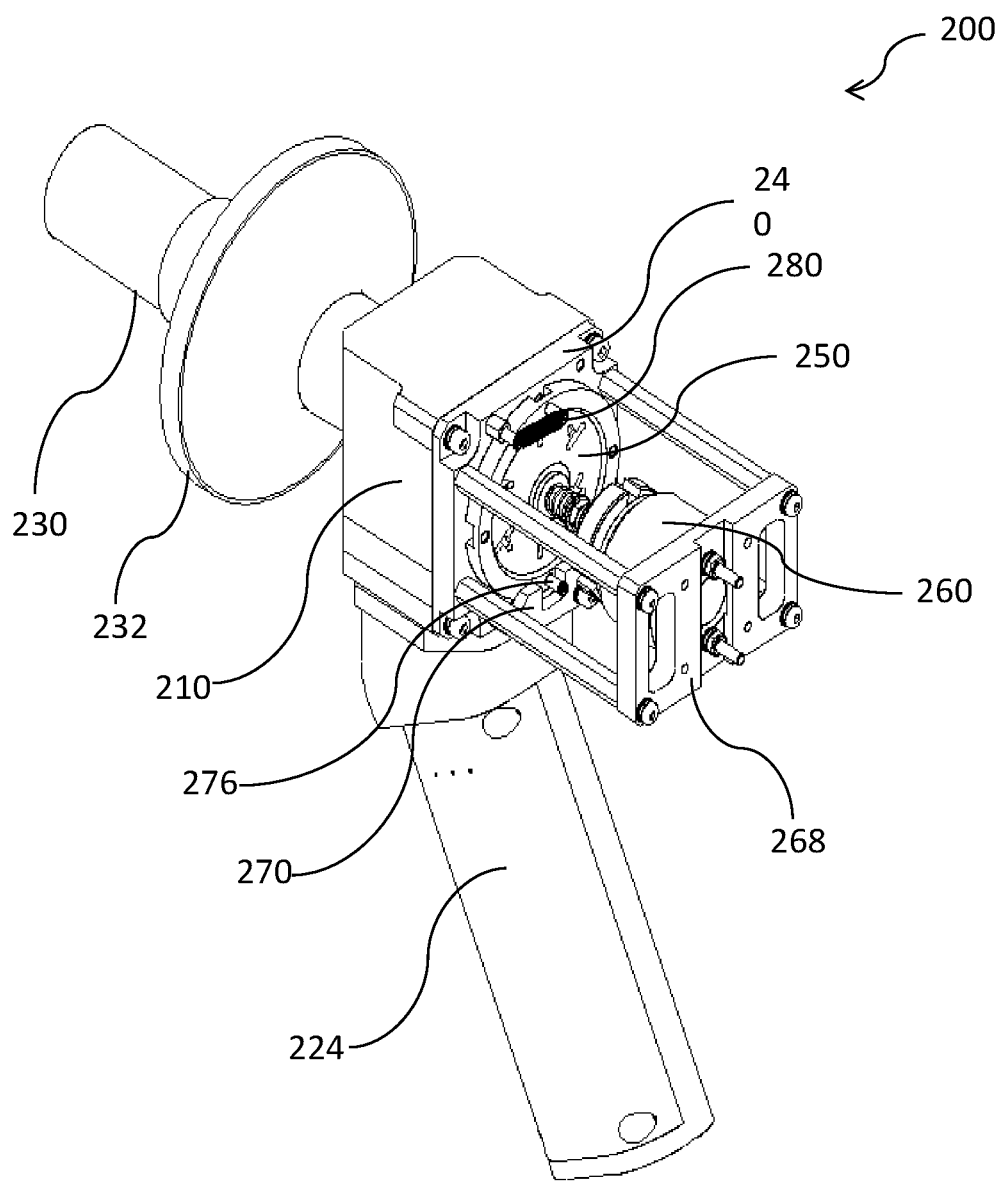
Figure 3:
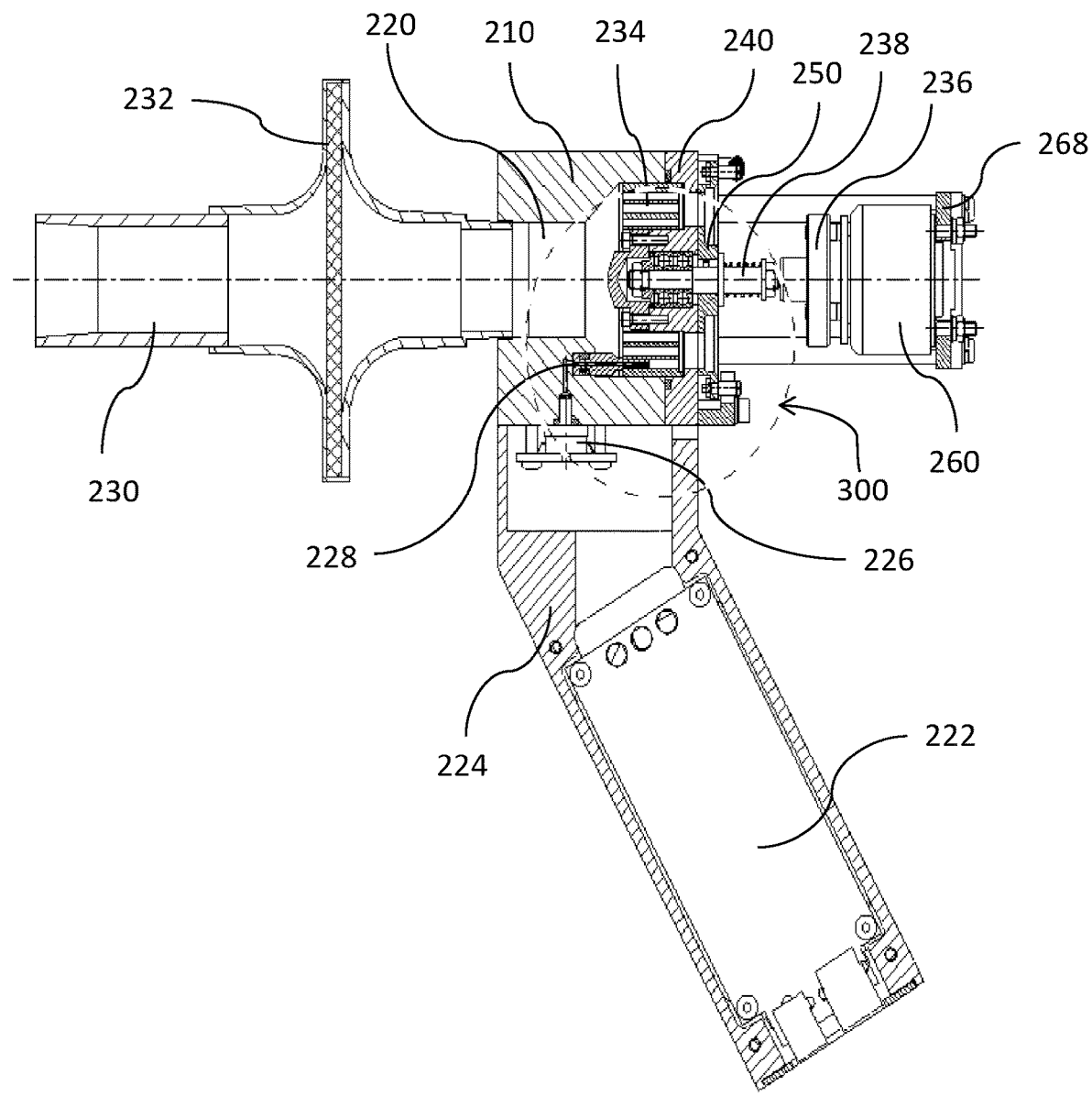
FIG. 3 constitutes a cross-sectional view of the pulmonary function test device that is illustrated in FIG. 2.
Figure 4:
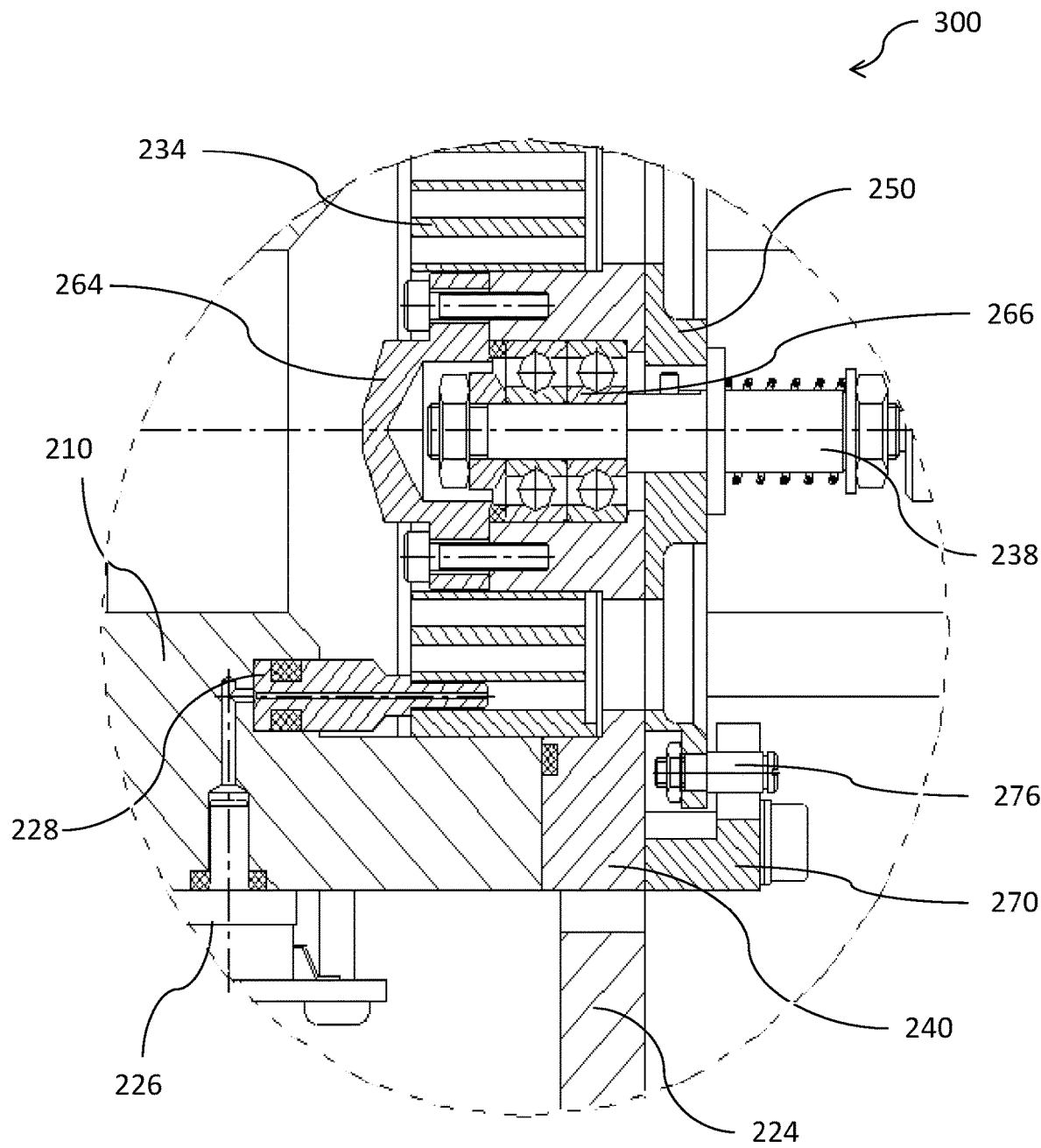
FIG. 4 constitutes a partial cross-section view A that is marked in FIG. 3.

Reference is now made to FIGS. 2-4. FIG. 2 constitutes a view in perspective of a pulmonary function test device 200 in accordance with some embodiments. FIG. 3 constitutes a cross-sectional view of the pulmonary function test device 200 in accordance with some embodiments. FIG. 4 constitutes a partial cross-section view 300 that is marked in FIG. 3 in accordance with some embodiments. Mouthpiece 230 may be mounted on the gas inlet port 230 (see FIG. 3) of the main chamber 210, serving as an interface between a subject and the pulmonary function test device 200, in accordance with some embodiments. Mouthpiece 230 is disposable, in accordance with some embodiments. Mouthpiece 230 comprises an anti-bacteriological filter 232, in accordance with some embodiments. A handle 224 may be configured to manually holding the device 200 while being used, in accordance with some embodiments. A shutter assembly may comprise a distal element 240, a shutter module 250, an extension spring 280, a shutter break 270, also termed hereinafter a hard stop, and a shutter pin 276 (see FIG. 4).

In accordance with some embodiments, the shutter module 250 may be in the form of a shutter wheel (see FIG. 2).

In accordance with some embodiments, the device is portable. In accordance with some embodiments, the device is hand held.

An actuator holder 268 may be mounted on the distal element 240 of the shutter assembly, in accordance with some embodiments. The shutter assembly may be mounted on the main chamber 210, in accordance with some embodiments. An actuator 260 may be mounted on the actuator holder 268.

The term "mounted on" as used herein, includes, but is not limited to coupled, assembled, bound, and/or attached.

In accordance with some embodiments, the actuator holder 268 is a rotary actuator holder, and the actuator 260 is a rotary actuator, wherein it may rotate the shutter wheel 250 when actuated or toggled.

Pressure transducer 226 is installed on main chamber 210 and may be connected via an orifice 228 to the internal space of a laminar flow diffuser 234 (see FIG. 3 and FIG. 4), in accordance with some embodiments.

Without being bound by any theory or mechanism, the inclusion of a laminar flow diffuser 234 in the main chamber 210, may create a laminar exhalation flow. Laminar gas exhalation, also termed herein 'flow', may improve the accuracy of the forced vital capacity (FVC) calculation.

It may be advantageous to use a pressure transducer 226 with a pressure resolution of at least 2 Pa, configured to operate in a temperature range of 0° C. to 50° C. and with a response time of at least 0.001 second, such as the following absolute pressure sensors: SDX Series by Honeywell, MPS-301A by JL World, SCP1000 Series by VTI Technologies or XP-6000CA by Epson Toyocom.

In accordance with some embodiments, gauge pressure transducers may be applied. However, in such cases a special algorithm should be used for calculation of the absolute pressure level. Examples of gauge pressure transducers may include 40PC by Honeywell, PX40 Series by Omega, and MPXV7007GC64 or MPXV5010GC6T1 by Freescale Semiconductor.

In accordance with some embodiments, the pressure transducer 226 may be enclosed within the handle 224.

In accordance with some embodiments, an electronic control module 222 may be enclosed within handle 224 (see FIG. 3). The control module 222 may be configured to supply one or more signals to a rotary actuator 260, in accordance with some embodiments, wherein said one or more signals will enable switching of the shutter module 250 from a first end position, wherein gas flows from the main chamber 210 to the atmosphere via shutter opening 152 having a total effective area $A_{S1}$, to a second end position wherein gas flows from the main chamber 210 to the atmosphere via shutter opening 154 having a total effective area $A_{S2}$.

The terms "total effective area $A_{S1}$" and "first total effective area $A_{S1}$" as used herein are interchangeable.

The terms "total effective area $A_{S2}$" and "second total effective area $A_{S2}$" as used herein are interchangeable.

In accordance with some embodiments, the control module 222 is configured to receive the one or more signals of the pressure transducer 226 and either store said one or more signals, transmit it to any external device, either by hardline or wireless connection, or perform both storage and transmission, wherein data transmission may occur either in real-time or post storage.

In accordance with some embodiments, the control module 222 may process the one or more input signals of the pressure transducer 226, wherein said processed signals are either stored, transmitted to any external device, either by hardline or wireless connection, or both stored and transmitted, wherein data transmission may occur either in real-time or post storage.

In accordance with some embodiments, the handle 224 is designed in its size and shape so that the device may be handheld comfortably.

In accordance with some embodiments, the orifice 228 may be located distal to the laminar flow diffuser 234, such that it is measuring the pressure in a space caged between the laminar flow diffuser 234 and the distal element 240.

In accordance with some embodiments, main chamber 210 will not include a laminar flow diffuser 234, wherein pressure transducer 226 may measure pressure directly in the space caged within the main chamber 210.

The rotary actuator 260 may rotate the shutter wheel 250 via the coupling 236 and shaft 238. A hard stop 270 includes a groove, in which a shutter pin 276 is allowed to maneuver within its boundaries, and which is mounted on the shutter wheel 250. The shaft 238 may have a bearing unit 266, which is mounted on distal element 240 (see FIG. 4), in accordance with some embodiments. The bearing protection cover 264 protects the bearing unit 266 from being exposed to the exhaled gas flow.

In accordance with some embodiments, the rotary actuator 260 should overcome the torque $M_{RA}$ that counteracts the rotation of the shutter wheel 250, according to the following formula:

$$M_{RA} = M_{FF} + M_{RS} + M_{AF}$$

where $M_{FF}$ is the friction torque between the shutter wheel 250 and the distal element 240, $M_{RS}$ is the torque of the extension spring 280, and $M_{AF}$ is the moment of inertia of the shutter wheel 250.

It may be advantageous to use one of the following two types of the rotary actuators: stepper motor or rotary solenoid. An example of a suitable stepper motor is model NEMA 14HS10-0404S by STEPPERONLINE. Examples of suitable rotary solenoids are model M341-30-180-R by GEEPLUS, and model 3EVM by LEDEX.

Figure 5A:
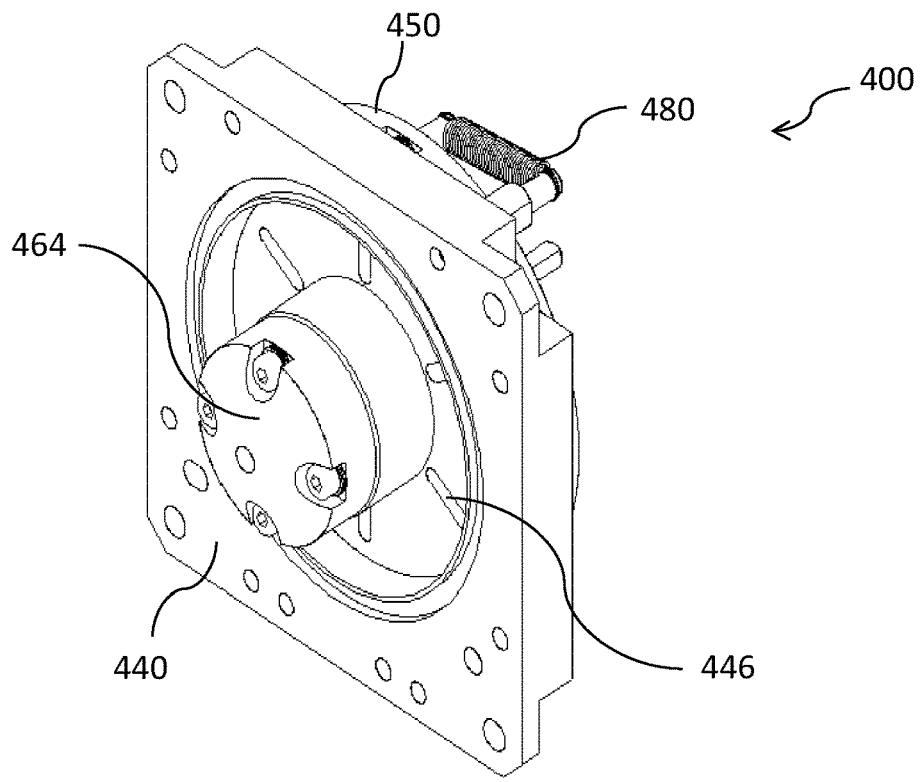
FIG. 5a constitutes a perspective front view of a shutter assembly, in accordance with some embodiments.
Figure 5B:
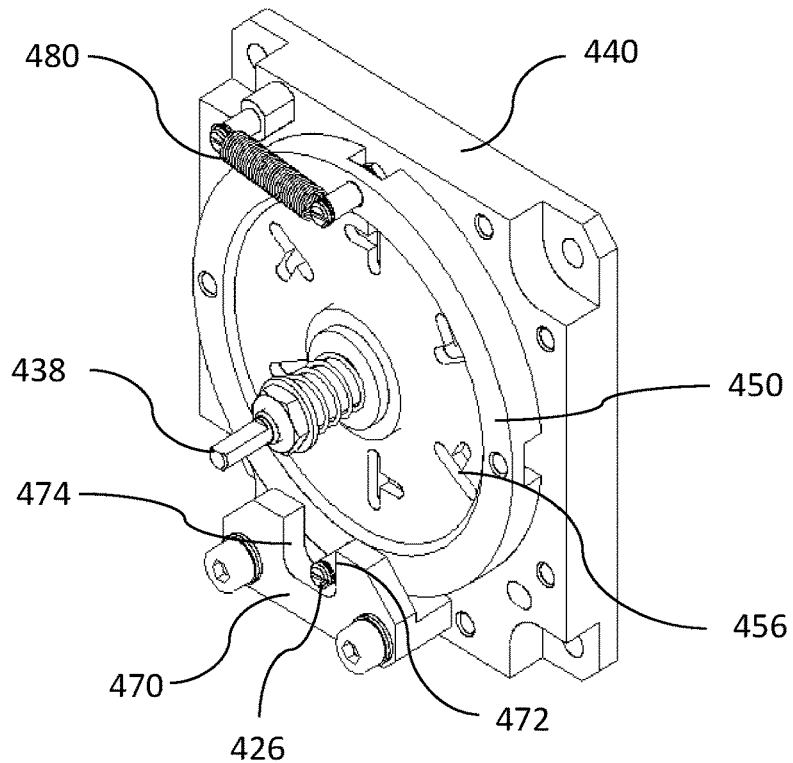
FIG. 5b constitutes a perspective back view of a shutter assembly, in accordance with some embodiments.

Reference is now made to FIGS. 5a-b. FIG. 5a constitutes a perspective front view (facing the gas inlet port 220) of a shutter assembly 400, while FIG. 5b constitutes a perspective back view (facing the actuator 260) of same shutter assembly 400. The distal element 440 may have, in the example illustrated in FIG. 5a, six distal openings 446 in the form of straight slots. The shutter wheel 450 may have the same number (six) of shutter openings 456 shaped in the form of a "T" (see FIG. 5b).

It is to be understood that the number of distal openings 446 on the distal element 440 or shutter openings 456 on the shutter wheel 450 may vary.

In accordance with some embodiments, the device comprises at least one distal opening 446.

In accordance with some embodiments, the device comprises at least one shutter opening 456.

In accordance with some embodiments, the number of distal openings 546 and the number of shutter opening 456 is identical.

In accordance with some embodiments, the number of distal openings 446 is different from the number of shutter opening 456.

A hard stop 470 includes a groove, in which a shutter pin 426 is allowed to maneuver within its boundaries, and which is mounted on the shutter wheel 450. The movement of shutter pin 426 is bounded between the groove's opposite sidewalls 472 and 474 (see FIG. 5b), which provide the limitation of the shutter wheel's 450 angle of rotation. In a first state of the shutter wheel, when the rotary actuator 260 is not toggled, the extension spring 480 exerts force on the shutter wheel 450, so as to rotate it counterclockwise until it reaches a stop position ("first end position") due to the shutter pin's 426 inability to move beyond the hard stop's first edge 472.

When the shutter wheel 450 is positioned in a first end position, a first gas flow-flows from the distal openings 456 through the shutter openings 446 to the atmosphere.

Figure 6A:
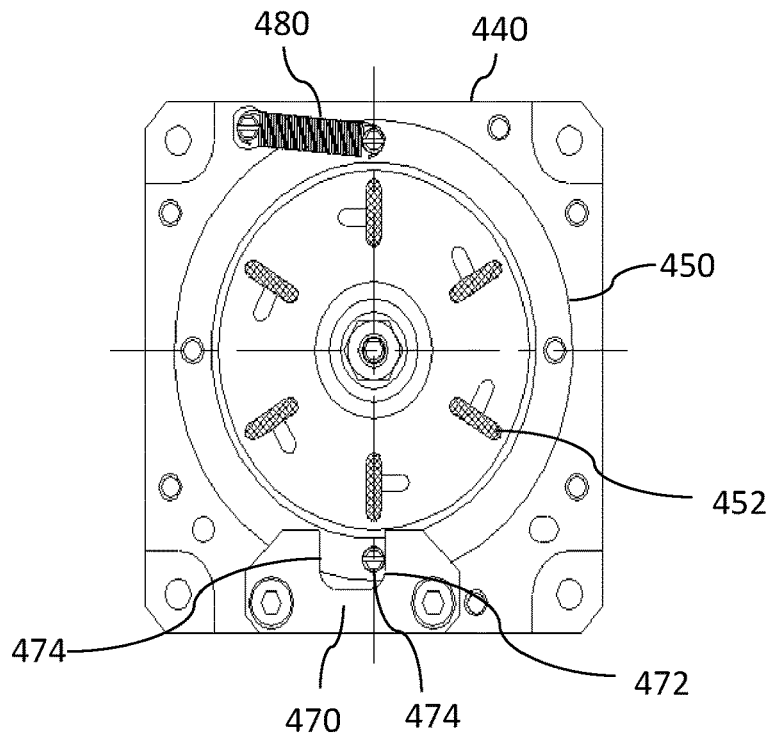
FIG. 6a constitutes a back view of a shutter assembly, in accordance with some embodiments, in a state of a first end position.
Figure 6B:
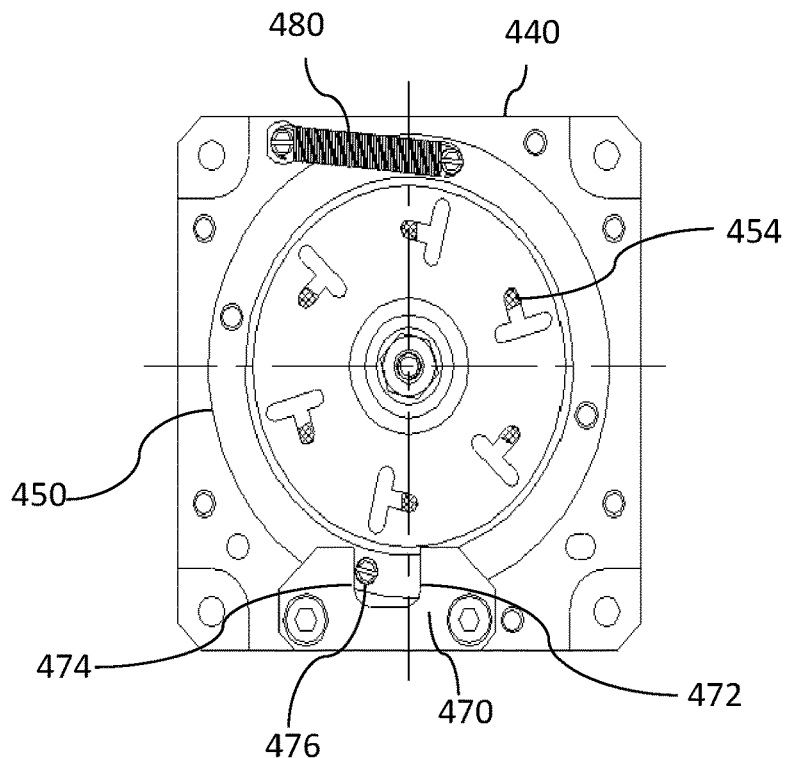
FIG. 6b constitutes a back view of a shutter assembly, in accordance with some embodiments, in a state of a second end position.

Reference is now made to FIGS. 6a-b. FIG. 6a constitutes a back view (facing the actuator 260) of a shutter assembly 400 in a state of a first end position. FIG. 6b constitutes a back view of a shutter assembly 400 in a state of a second end position. In the first end position illustrated in FIG. 6a, six shaded areas 452, together forming a total effective area $A_{S1}$, indicate the area through which passage of exhaled gas flow occurs in this state. When the rotary actuator 260 is actuated or toggled, it rotates the shaft 438 with the shutter wheel 450 until the shutter pin 426 is in contact with the hard stop's second edge 474, reaching a second end position illustrated in FIG. 6b. The six shaded areas 454 form together a total effective area $A_{S2}$. The total effective area $A_{S2}$ indicates the area through which a passage of exhaled air occurs and is also termed hereinafter 'a second gas flow'. The first gas flow and the second gas flow, corresponding to effective areas $A_{S1}$ and $A_{S2}$, respectively, are affecting the device's resistance to gas flow exhalation.

In accordance with some embodiments, the distal element 440 and shutter wheel 450 may comprise distal openings 446 in the shape of straight slots and shutter openings 446 in the form of "T" shaped windows, respectively (see FIGS. 5a-b).

In accordance with some embodiments, distal openings 446 and shutter openings 456 may have any shape or size, wherein the resulting areas $A_{S1}$ and $A_{S2}$ are different. In a preferred embodiment, distal openings 446 and shutter openings 456 are configured so that $A_{S1} > A_{S2}$, that is to say that the flow resistance in the first end position, in which the total effective air channel area is $A_{S1}$, is lower than the flow resistance in the second end position, in which the total effective air channel area is $A_{S2}$.

Figure 7A:
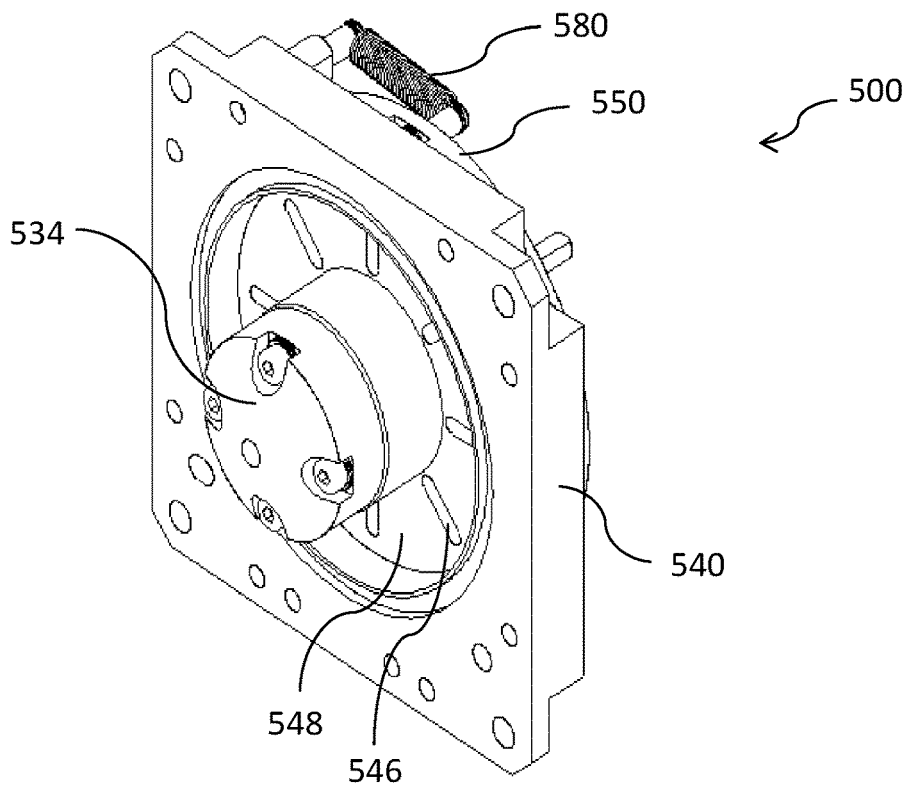
FIG. 7a constitutes a perspective front view of a shutter assembly, in accordance with further embodiments.
Figure 7B:
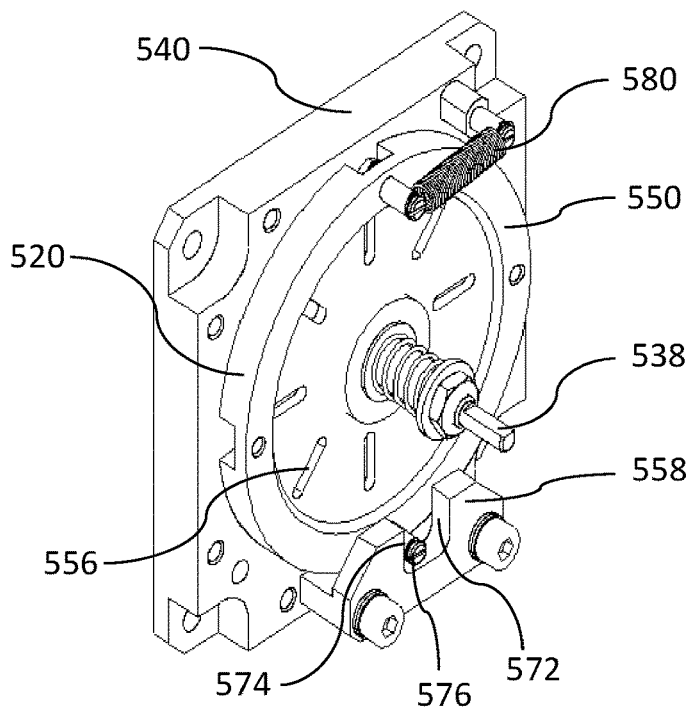
FIG. 7b constitutes a perspective back view of a shutter assembly, in accordance with further embodiments.

Reference is now made to FIGS. 7a-b. FIG. 7a constitutes a perspective front view (facing the gas inlet port 220) of a shutter assembly 500, while FIG. 7b constitutes a perspective back view (facing the actuator 260) of same shutter assembly 500, in accordance with some embodiments. The distal element 540 may have, in the example illustrated in FIG. 7a, eight oval distal openings 546. The shutter wheel 550 may have the same number (eight) of the oval shutter openings 546 (see FIG. 7b), which are essentially identical, meaning that they are of the same size and shape.

It is to be understood that the number of distal openings 546 on the distal element 540 or shutter openings 556 on the shutter wheel 550 may vary.

In accordance with some embodiments, the device comprises at least one distal opening 546.

In accordance with some embodiments, the device comprises at least one shutter opening 556.

In a first state of the shutter wheel 550, when the rotary actuator 260 is not actuated nor toggled, the extension spring 580 exerts force on the shutter wheel 550, so as to rotate it clockwise until it reaches a stop position ("first end position") due to the shutter pin's 576 inability to move beyond the hard stop's 558 second edge 574. In this position, distal openings 546 are positioned opposite to the shutter openings 556. In the first state the exhaled gas flow (first gas flow) flows through the shutter openings 556, thereby forming effective area $A_{S1}$.

When the rotary actuator 260 is actuated or toggled, it rotates the shaft 538 with the shutter wheel 550 until the shutter pin 576 is in contact with the hard stop's first edge 572, reaching a second end position. In accordance with some embodiments, at least one of the shutter openings 556 is situated opposite to the smooth distal element wall 548 (see FIG. 7a). In the second end position the exhaled gas flow (second gas flow) flows through a portion of shutter openings 556 positioned opposite to distal openings 546, thereby forming effective area $A_{S2}$.

In accordance with some embodiments, the device comprises an open gap (not shown) between the shutter wheel 550 and distal element 540, configured to allow gas flow from the distal opening 546 through the circumference of said gap, both at first end position and second end position. In accordance with some embodiments, the first state the exhaled gas flow (first gas flow) flows through the shutter openings 556, and through the open gap between shutter module 550 and the distal element 540, thereby forming effective area $A_{S1}$.

In accordance with some embodiments, the number and position of distal openings 546 is configured so that in the second end position, some of the shutter openings 556 are situated opposite to the smooth distal element's wall 548, while the remaining shutter openings are positioned against opposing distal openings 546, in a manner that the perimeters of shutter openings—556 through which passage of exhaled gas occurs in this state together with the perimeter of the shutter wheel 550 multiplied by the depth of the gap between shutter wheel 550 and distal element 540 (forming the total circumferential area of said gap), are forming together the total effective area $A_{S2}$.

In accordance with some embodiments, all of the shutter openings 556 are situated opposite to the smooth distal element's wall 548 in the second end position, such that the effective area $A_{S2}$ is only the area of the perimeter of shutter wheel 550 multiplied by the depth of the gap between shutter wheel 550 and distal element 540 (forming the total circumferential area of said open gap).

It is to be understood that at all states passage of airflow is available. During second end position, the passage is restricted in comparison to the passage during the first end position, such that only a portion of shutter openings is positioned opposite to distal openings. This relative restriction is also referred to as relative limitation.

In accordance with some embodiments, the device further comprises at least one shutter edge opening (not shown) located on the shutter module edge 520, wherein the at least one shutter edge opening is configured to allow gas flow from the distal opening 546 through the circumference of the at least one shutter edge opening, both at first end position and second end position.

It should be understood that $A_{S2}$ is always a positive value, meaning that gas flow to the atmosphere must occur at second end position, either through at least one shutter opening 556, the gap between shutter wheel 550 and distal element 540, at least shutter edge opening, or any combination thereof.

In accordance with some embodiments, the area $A_{S2}$ is in the range of 20% and 40% of the area $A_{S1}$. It is to be understood that the relationship between $A_{S2}$ and $A_{S1}$ is not limited to the aforementioned ratios. In fact, the relationship between $A_{S2}$ and $A_{S1}$ may vary.

In accordance with some embodiments, as exemplified in FIGS. 5a-b and 6a-b, extension spring 480 is located such that it exerts force on the shutter wheel 450, which rotates it counterclockwise until shutter pin 426 is in contact with the hard stop first edge 472, designating such position as first end position, while the other position, in which the shutter pin 426 is in contact with the hard stop second edge 474 is designated as second end position.

In accordance with some embodiments, as exemplified in FIGS. 7a-b, extension spring 580 is located such that it exerts force on the shutter wheel 550, which rotates it clockwise until shutter pin 576 is in contact with the hard stop's second edge 574, designating such position as first end position, while the other position, in which the shutter pin 576 is in contact with the hard stop first edge 572 is designated as second end position.

It should be noted that additional technical solutions may be used by those skilled in the art to improve and extend some features of the device. For example different shutter module designs and displacement mechanisms, which may or may not be formed as circular elements, can be utilized to achieve different gas outlet, namely, different effective areas or resistances, between first end position and second end position of said shutter module.

The term "displacement" as used herein refer to a reposition, or change in position of the shutter module. The change is typically movement of the shutter module between two locations, where the distance between the position prior to displacement and the position post displacement has a range.

The terms "displace", "displacing", "toggle" and "toggling" are interchangeable and refer to the operation that induces, or causes, displacement.

A control system (not shown) of the pulmonary function test device is configured to perform at least the following two main functions: data acquisition and data processing. The control system may be situated within the device, for example as part of the control module 222 (see FIG. 3), or as part of an external computer system, for example as a personal computer or laptop, wherein external computer system is in communication (either hardline or wireless) with the device. Both functions may be controlled by a computer system and a microprocessor firmware in communication with each other. During data acquisition, shutter module 250 is displaced due to one or more signals derived from patterns of acquired pressure signals, which in turn change the resistance to exhaled gas flow. An operator may initiate the operation process by providing an initiation command via software tool installed on a computer system, in accordance with some embodiments. A computer system may send commands, which may be related to initialization parameters, to an internal microprocessor through wireless (e.g. Wi-Fi, Bluetooth, near field communication, and the like) or hardline (e.g. serial, parallel, universal serial bus, and the like) communication means, which initiate data acquisition and data processing.

A signal from the pressure transducer may be digitized, for example, by 12 bits A/D converter with a predefined sample rate, and transmitted back to a computer system over, for example, USB protocol during a predefined time period. At the same time, the microprocessor processes the acquired pressure signal patterns and determines peak values and signal slope directions. When a signal's first peak followed by a signal's decay are determined, and the acquired values fall below a predefined threshold value, the microprocessor triggers an output signal to toggle shutter module displacement, changing the total effective area as cited above. A computer system may receive acquired data of the pressure signals in a continuous manner during the complete duration of the measurement process.

Data processing may be performed once all pressure data, composed of all acquired pressure signals during a measurement process, is transmitted to a computer system. The processing may contain, but is not limited to, the following steps: a digital filtration procedure, conversion of acquired pressure signals to absolute pressure values based on a pressure transducer calibration data, determination of the signal base flow, and determination of a start and finish points of a forced gas exhalation process. Additional steps of the processing may include, yet are not limited to, determination of the first and second pressure signal peaks, running algorithms and mathematical calculations, including such that are based on related values approximations and logical assumptions, as will be presented here forth, and a first and second peak of pressure signals.

The main clinical objectives of respiratory function tests are to provide diagnosis, assessment of severity, treatment monitoring and evaluation of prognosis. Spirometry measures vital capacity and force expiratory volume in one second. These parameters permit differentiation between restrictive and obstructive respiratory diseases. The spirogram flow-volume curves are used for diagnostics.

Figure 8:
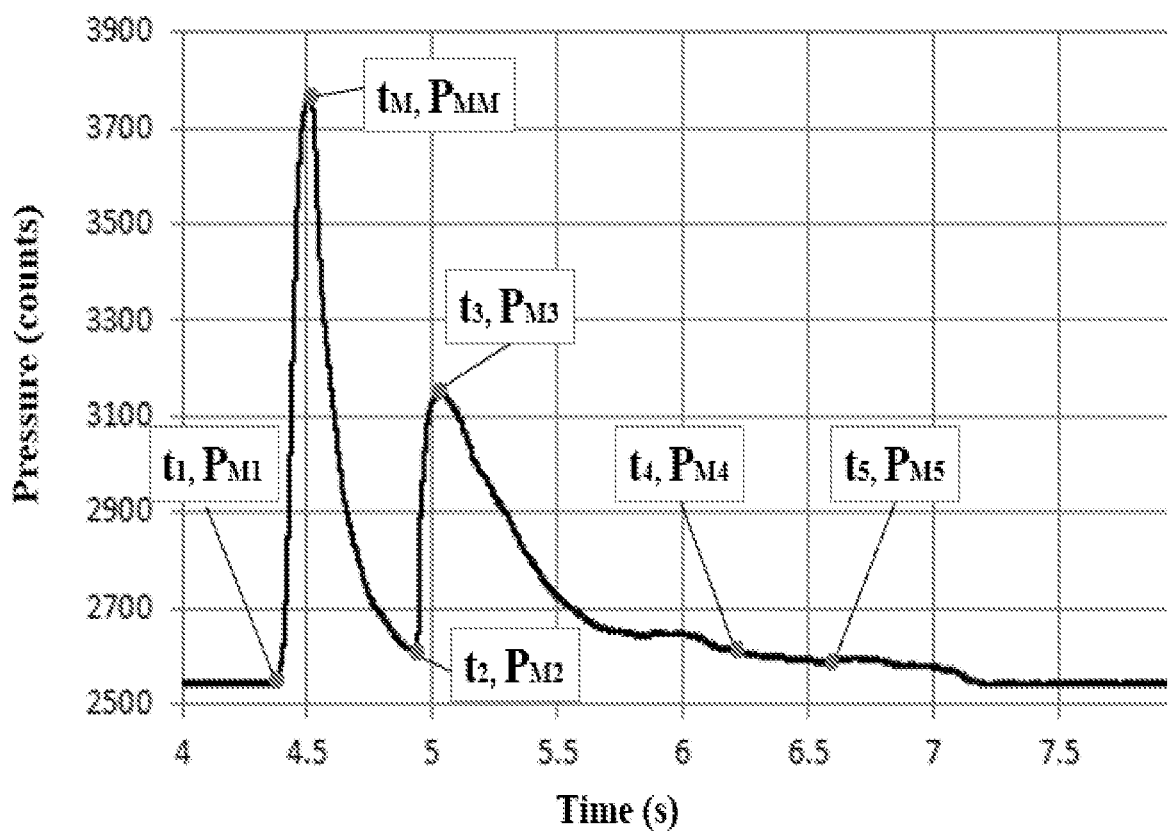
FIG. 8 shows an example of a graph of gauge pressure reading over time during a sequential forced gas exhalation event, in accordance with some embodiments.

Reference is now made to FIG. 8, which shows an example of a graph of gauge pressure reading over time during a sequential forced gas exhalation event, in accordance with some embodiments. The time $t_1$ represents the starting point of the forced gas exhalation, and time $t_5$ represents the end of said forced gas exhalation. The pressure at $t_5$ is $P_5$, also termed "end point pressure". In accordance with some embodiments, $t_5$ at which the end point pressure is identified, is based on estimations as further detailed herein. Proper determination of the duration of the forced exhalation, i.e. the time between $t_1$ and $t_5$, may result in more reliable estimation of total lung capacity, as will be described here forth. In most conventional spirometry tests, the back extrapolation approach, which is well known to those skilled in the art, is used for determination of a start point $t_1$. This approach may be used for the pulmonary function test device in accordance with some embodiments, wherein the start of the process is set to be at point $(t_1, P_{M1}$; see FIG. 8). A second approach for determination of the start point $(t_1, P_{M1})$ may be the pressure threshold method, according to which:

$$P_{M1} = P_A + \Delta P_1$$

where $P_A$ is the atmospheric pressure, and $\Delta P_1$ is a predetermined pressure threshold, which in accordance with some embodiments may be set as $\Delta P_1 = 50$ Pa. Such a method for determining the start of the forced gas exhalation may be prone to errors associated with the use of an arbitrarily predetermined threshold. Nevertheless, the approach is known in the art and may be considered acceptable with a sufficient accuracy despite said errors. Other methods for determination of the start point $(t_1, P_{M1})$ may be used in the context of this disclosure.

The second point to be evaluated on the graph of pressure vs. time (see FIG. 8) is the point of first pressure peak $(t_M, P_{MM})$. The first pressure peak $(t_M, P_{MM})$ may be determined by any known method in the art for determining a peak maximum in a graph, implemented on pressure data acquired during the operation of the device.

When pressure drops to $(t_2, P_{M2}$; see FIG. 8), an actuation signal, also referred to as a toggling signal, is transmitted to initiate the shutter module's displacement from first end position to second end position, wherein upon displacement the first flow, also referred to as flow rate', of exhaled gas, corresponding to the effective area $A_{S1}$, changes to a second flow rate of exhaled gas, corresponding to the effective area $A_{S2}$. The pressure point $P_{M2}$ may depend on the values of effective areas $A_{S1}$ and $A_{S2}$, and may be roughly estimated, in accordance with some embodiments, by the following formulas:

$$P_{M2} = P_A + \Delta P_2$$

where $\Delta P_{M2}$ may be calculated as:

$$\Delta P_{M2} = \frac{0.01 \cdot P_A \cdot A_{S2}}{A_{S1}}$$

The point $(t_3, P_{M3})$ represents a second pressure peak in the region between point $(t_2, P_{M2})$ and pressure volume indicator point $(t_4, P_{M4})$. Determination of this point may be performed by known methods in the art. This point may be used for calculating gas flow resistance and volumetric characteristics.

In pressure volume indicator point $(t_4, P_{M4})$ the pressure may be equal to the pressure in the point $(t_2, P_{M2})$, that is $P_{M4} = P_{M2}$. This point may be used for calculating volumetric characteristics.

The point $(t_5, P_{M5})$ represents the end of forced gas exhalation. This point may be determined, in accordance with some embodiments, by the deviation method, whereby forced exhalation is finished when the mouth pressure deviation is less than or equal to $\dot{P}_{M5F}$, which may be estimated according to the following formula:

$$\dot{P}_{M5F} = \frac{0.1 \cdot (P_{M4} - P_{M3})}{t_4 - t_3}$$

In accordance with some embodiments, assuming that a maximal duration of forced or spontaneous gas exhalation for healthy subjects may be in the range of 4-6 seconds; and for subjects with airways obstruction or subject of older age, maximal duration of gas exhalation may typically be in the range of 6-8 seconds, it may be acceptable to assume a maximal recording time of pressure data as $T_{REC} = 15$-$20$ s. In accordance with some embodiments, the sampling rate of the pressure signals may be at least 1000 Hz (such that the sampling time is not higher than $t_S = 0.001$ s). In accordance with some preferred embodiments, sampling rate may be at least 5000 Hz (such that the sampling time is not higher than $t_S = 0.0002$ s), so that the minimal size of the memory module of the pressure transducer recording can be calculated according to the formula:

$$N_M = T_{REC}/t_S$$

For embodiments where the sampling rate is 5000 Hz, minimal required size for the memory module is $N_M = T_{REC}/t_S = 100{,}000$ points.

Figure 9:
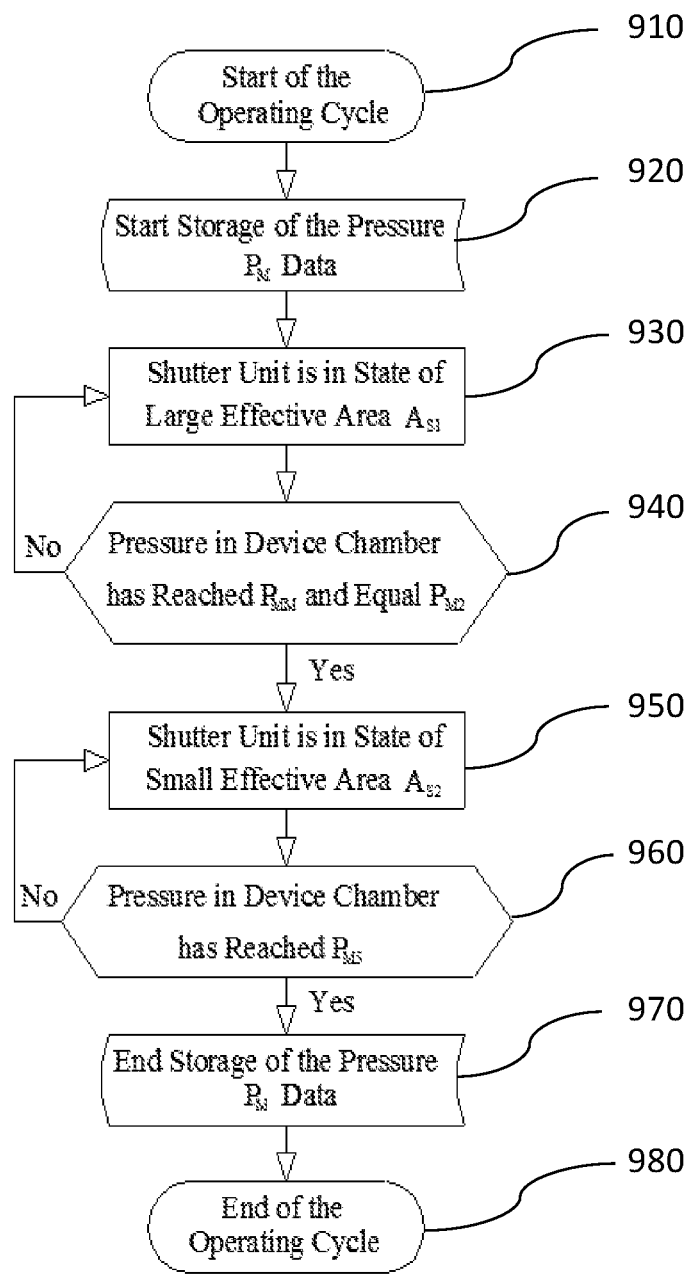
FIG. 9 shows a flowchart of the system operation mode, in accordance with some embodiments.

Reference is now made to FIG. 9, which shows a flowchart of the system's operation mode, in accordance with some embodiments. First, the operating cycle of the device is started (step 910), which may be triggered, in accordance with some embodiments, by an operator of the system. From that moment, pressure $P_M$ within main chamber 210, measured by the pressure transducer 226, is stored (step 920) either in a memory module within the device, or in a memory module of a computer system, after being transmitted (either by hardwire or wireless transmission) thereto. The shutter module 250, from the beginning of the measurement process, and while not being actuated or toggled, is in a first end position, wherein exhaled gas flows to the atmosphere through first passage, corresponding to the effective area $A_{S1}$ (step 930). Data processing identifies when first peak pressure $P_{MM}$ has been reached, after which the control system checks whether the pressure reached the level $P_{M2}$ (step 940) or is within the range of that level. As long as the pressure has not reached the first peak $P_{MM}$, or has not reached the level $P_{M2}$ after reaching $P_{MM}$, or has not reached pressures within the range of those levels, shutter module 250 remains in first end position. At the moment the pressure reaches $P_{M2}$, or is within the range of that level, after reaching first peak pressure $P_{MM}$, a signal may be sent to the actuator 260, such that, as a result the actuator 260 displaces, or induce displacement of, shutter module 250 to a second end position, wherein exhaled gas flows to the atmosphere through second passage, corresponding to the effective area $A_{S2}$ (step 950). From that point, data processing identifies when second peak pressure $P_{M3}$ has been reached, after which the control system checks whether the pressure is within the range of the level $P_{M5}$ (step 960). As long as pressure has not reached the second peak $P_{M3}$, or has not reached the level $P_{M5}$ after reaching $P_{M3}$, shutter module 250 remains in second end position. At the moment that the pressure reaches the level $P_{M5}$, after reaching second peak pressure $P_{M3}$, pressure data storage stops (step 970), and the operation cycle of the system ends (step 980), which may include the return of shutter module 250 to a state of first end position.

The terms "threshold" and "level" as used herein are interchangeable.

Typical parameters determined by spirometry include, but are not limited to, any one or more of the following:

1) Spirometric Characteristics defined by forced expiratory flow parameters (spirogram). The main spirometric parameters are: Forced vital capacity (FVC); volume of gas exhaled in the first one second of exhalation (FEV1); forced expiratory flow between 25 and 75 percent of FVC (FEF25-75) i.e. the average expired flow over the middle half of FVC manoeuver; and peak expiratory flow (PEF).

2) Lung Volumetric Parameters: Total lung capacity (TLC); residual volume (RV) i.e. the volume of gas remaining in the lung after maximal exhalation; and thoracic gas volume (TGV) i.e., the absolute volume of gas in thorax at any point in time and any level of alveolar pressure.

3) Airway Resistance defined as the ratio of driving pressure to the rate of air flow. Resistance to flow in airways depends on whether the flow (laminar or turbulent), on the dimensions of an airway and on a viscosity of a gas. Total resistance to air flow includes three main components: (a) inertia of respiratory system (contributes negligibly to total resistance), (b) tissue resistance of lungs and chest walls (accounts for approximately 20% of total resistance), and (c) airway resistance ($R_{AW}$) defined as the ratio of driving pressure to the rate of air flow (80% of total resistance).

4) Lung Compliance, or pulmonary compliance, refers to the extensibility of the lungs. It is expressed as a change in volume divided by a change in pressure. There are two types of lung compliance: static and dynamic. Static compliance of lungs is the change in volume for a given change in transpulmonary pressure with zero gas flow. Dynamic lungs compliance is compliance of lungs at any given time during actual movement of air.

The graph of pressure vs. time (see FIG. 8) is processes to derive at least one value related to at least one pulmonary function characteristics of the tested subject, such as Thoracic Gas Volume (TGV) and Total Lung Capacity (TLC), by applying the appropriate formulas. In accordance with some embodiments, a mathematical model of the pulmonary function test device considers two chambers: first camber represents is lung that has a varying volume TGV, and second chamber has constant volume $V_D$, wherein $V_D$ is the sum of the following two volumes: the internal volume of the pulmonary function test device 100 $V_{STS}$, and the anatomic dead-space volume $V_{DA}$, wherein the volume $V_D$ may be assumed to be constant between the biological bronchial airway resistance (not shown) and shutter module 150. The anatomic volume $V_{DA}$ may be evaluated, for healthy individuals, as $V_{DA}=W_P \cdot K_V$, where $W_P$ is patient weight in kg, and $K_V$ is proportional coefficient that is $K_V=2.2 \cdot 10^{-6} m^3/kg$. The internal volume of the pulmonary function test device may be defined as a sum of volumes $V_{STS}=V_F+V_{MT}+V_{AT}+V_M$, wherein $V_{MT}$ is the volume of the mouth tube, $V_F$ is the biological filter internal volume, $V_{AT}$ is the volume of the adapter tube, and $V_M$ is the internal volume of the pulmonary function test device (see FIG. 1). In accordance with some embodiments, the mathematical model may further rely on the following assumptions: the exhaled air is the perfect gas; the first law of thermodynamics may be used for describing the pressure changing process in the pulmonary system and the pulmonary function test device; the pressure and temperature within the pulmonary function test device chambers and pulmonary system are homogeneous; and that the process may be assumed to be isothermal.

The differential equations of the mathematical model are:

$$\begin{cases} \dot{P}_L = \frac{1}{TGV} \cdot [P_L \cdot Q_L - G_R \cdot R \cdot T] \\ \dot{P}_M = \frac{R \cdot T}{V_D} \cdot (G_R - G_S) \end{cases}$$

where $P_L$ is the absolute pressure in the lung (alveoli), $P_M$ is the absolute pressure in the constant volume $V_D$, $Q_L$ is lung flow rate, $G_R$ is airway resistance mass flow rate, $G_S$ is shutter module mass flow rate, R is gas constant, T is exhalation gas temperature.

The graph of pressure vs. time (see FIG. 8) may be further processes to estimate key indices employed in a typical pulmonary function test. The standard measured indices commonly measured by typical pulmonary function test devices are Forced Vital Capacity (FVC), Forced Expired Volume in 1 second (FEV1), Forced Expiratory Flow between 25 and 75 percent of FVC (FEF25-75%), and Peak forced Expiratory Flow (PEF).

FVC is the volume of gas, which is expired during a forced exhalation. FVC may be estimated as $FVC=FVC_1+FVC_2$, wherein $FVC_1$ may be calculated in the sample interval of the pressure measurement between point $t_1$ and $t_2$ as a function of effective area $A_{S1}$, and $FVC_2$ may be calculated in the sample interval of the pressure measurement between points $t_2$ and $t_5$ as a function of effective area $A_{S2}$.

FEV1 is the volume exhaled in first second of forced exhalation.

FEF25-75% is the average expired flow rate during the exhalation time period between 25% and 75% of the FVC. Estimation of FEF25-75% may be calculated according to the following formula:

$$FEF_{25-75\%} = \frac{\Delta t \cdot \sum_{j=N25}^{j=N75} Q_j}{t_{75} - t_{25}}$$

where $\Delta t$ is sample time interval, Q is the flow rate, which may be estimated as a function of the atmospheric pressure, the absolute pressure in the main chamber 110, and outlet area $A_S$, wherein:

$$\begin{cases} A_S = A_{S1}, & \text{for } t_1 \le t \le t_2 \\ A_S = A_{S2}, & \text{for } t_2 < t \le t_5 \end{cases}$$

where $t_{25}$ is the time at which the forced vital capacity is $0.25 \cdot FVC$, and $t_{75}$ is the time at which forced vital capacity is $0.75 \cdot FVC$, and where $N25 = t_{25}/\Delta t$, $N75 = t_{75}/\Delta t$ PEF is the maximum value of the exhaled flow, which is estimated on the basis of the flow rate Q as cited above, at the maximum point $(t_M, P_{MM})$.

The shape of the pressure vs. time graph (see FIG. 8) may vary from subject to subject. Moreover, analysis of different indices of the curve may be indicative of the medical condition of a subject, as such curves may differ between healthy subjects, patients suffering from restrictive ling disease and patients suffering from obstructive lung disease. Several groups of indices, in accordance with some embodiments, may be calculated in order to test whether they can be used to produce a diagnostic event, by analyzing their associations with and diagnose the subjects' pulmonary conditions. These groups are: time related indices, volume related indices, and pressure, as well as pressure with volume, related indices.

The group of time related indices may include, but is not limited to, the following indices:

$$TI = \frac{t_4 - t_3}{t_4 - t_1}$$

is time index $$TC_1 = \frac{t_3 - t_2}{t_5 - t_2}$$

is the first time coefficient $$TC_2 = \frac{t_5 - t_3}{t_5 - t_1}$$

is the second time coefficient $$TC_3 = \frac{t_2 - t_1}{t_5 - t_2}$$

is the third time coefficient

The group of volume related indices may include, but is not limited to, the following indices:

$$VI = \frac{(VC_4 - VC_2) \cdot TLC_{PR}}{VC_4 \cdot FEV1}$$

is volume index $$VCC_1 = \frac{VC_4 - VC_2}{VC_4}$$

is the first volume coefficient $$VCC_2 = \frac{FEV1}{VC_5}$$

is the second volume coefficient $$VCC_3 = \frac{VCC_1}{VI}$$

is the third volume coefficient

The group of pressure, and pressure with volume, related indices may include, but is not limited to, the following indices:

$$PI = \frac{P_{M3} - P_A}{P_{MM} - P_A}$$

is pressure index $TVI_O = 0.5 \cdot (TI + TC2 + VC3)$ is obstructive index where $VC_2$ is vital capacity at the time $t=t_2$ [m³], $VC_4$ is vital capacity at the time $t=t_4$ [m³], $VC_5$ is vital capacity at the time $t=t_5 (VC_5 \approx FVC)$ [m³], and $TLC_{PR}$ is predicted value of the TLC [m³], wherein $TLC_{PR}$ may be estimated by formulas that incorporate age, gender, height and weight.

The terms "Vital Capacity" or "VC" and "Forced Vital Capacity" or "FVC" are interchangeable.

The estimation of TGV and TLC, in accordance with some embodiments, may be performed by three algorithms. The main assumption of the first algorithm is that the derivative of the pressure $P_M$ along the graph of pressure vs. time varies linearly. In accordance with some embodiments, the derivative of $P_M$ may vary linearly between two points before and after $t_4$.

Stated otherwise, the first algorithm is based on the assumption that the derivative of the pressure versus time curve is linear during a period of time that encompasses $t_4$. This period includes $t_4$ nested between two predetermined time periods, occurring before and after $t_4$. The two time periods may be identical, similar or different from one another. According to the first algorithm the TGV and TLC may be estimated as:

$$TLC_1 = B_{11} \cdot \frac{\dot{P}_{M4} \cdot VC_4 - B_{12} \cdot A_{S2} \cdot \sqrt{P_A \cdot (P_{M4} - P_A)}}{\dot{P}_{M4}}$$

$$TGV_1 = TLC_1 - VC_4$$

where $\dot{P}_{M4}$ is pressure derivative in the constant volume $V_D$ at the time $t=t_4$, $B_{11}$ and $B_{12}$ are constant coefficients.

The main assumption of the second algorithm is the pulmonary function test device's pressure between two points along the graph of pressure vs. time may be approximated to an exponential curve. In accordance with some embodiments, the pressure between the second pressure peak and the end of the forced gas exhalation may be approximated to an exponential curve. According to the second algorithm the TGV and TLC may be estimated as:

$$TGV_2 = B_{21} \cdot A_{S2} \cdot (t_4 - t_3) \cdot \left[\ln\left(\frac{P_{M3} - P_A}{P_{M4} - P_A}\right)\right] \cdot \sqrt{\frac{P_{M4} - P_A}{P_{M3} - P_A}}$$

$$TLC_2 = TGV_2 + VC_4$$

where $B_{21}$ is constant coefficient.

The main assumption of the third algorithm is that the pulmonary function test device's pressure between two points along the graph of pressure vs. time may be approximated to a parabolic curve. In accordance with some embodiments, the pressure between the second pressure peak and the end of the forced gas exhalation may be approximated to a parabolic curve. According to the third algorithm the TGV and TLC may be estimated as:

$$TGV_3 = \frac{B_{31} \cdot (t_4 - t_3)^3}{3 \cdot \ln\left(\frac{P_{M4}}{P_{M3}}\right)} + \frac{B_{32} \cdot (t_4 - t_3)^2}{2 \cdot \ln\left(\frac{P_{M4}}{P_{M3}}\right)}$$

$$TLC_3 = TGV_3 + VC_4$$

where $B_{31}$ and $B_{32}$ is constant coefficients.

In accordance with some embodiments, TGV and TLC may be estimated as averages of the values calculated according to all three algorithms.

The estimation of airway resistance $R_{AW}$, in accordance with some embodiments, may be performed with assumption that during the switching between the shutter openings with effective area $A_{S1}$ and $A_{S2}$ the pressure varies only in the constant volume $V_D$, while in the lung volume the pressure remains constant or its changing is negligible. This assumption is based on the fact that the lung volume at least on the order of magnitude greater than the $V_D$ volume. Then the airway resistance may be evaluated as:

$$R_{AW} = \frac{(P_{L3} - P_{M3})}{Q_{L3}}$$

where $Q_{L3}$ is lung flow rate at the time $t=t_3$, $P_{L3}$ is the absolute pressure in the lung (alveoli) at the time $t=t_3$, which may be estimated as:

$$P_{L3} = \frac{(P_{M3} - P_{M2}) \cdot (1 - 2 \cdot B_R)}{1 - B_R},$$

wherein $B_R$ is constant coefficient.

The estimation of lung compliance $C_{LT}$, in accordance with some embodiments, may be performed using the time constant parameter. A time constant of a compartment is a function of the compartment's resistance and compliance. The lung is assumed to behave as the compartment in the trial. The time constant $\tau_E$ expresses how quickly a compartment can react to pressure alteration and provides an indication of the filling or emptying velocity of a lung compartment. The lung consists of a large number of compartments with variable time constants. This heterogeneity is often exaggerated with lung disease, such as pneumonia or pulmonary fibrosis. Clearly, the more inhomogeneous the lung ventilation is, the wider the spectrum of regional time constants. This causes variation in the filling and emptying periods and the filling volumes for individual compartments. At a given pressure, a compartment with high resistance and good compliance fills slowly with a resulting large volume, which may be indicative of asthma, for example. Conversely, a compartment with poor compliance and low resistance fills quickly, resulting in a smaller volume, which may be indicative of pulmonary fibrosis, for example. Mathematically, the time constant is defined as compliance multiplied by the airway resistance, and the resulting value is given in units of seconds:

$$\tau_E = R_{AW} \cdot C_{LT}$$

where the time constant $\tau_E = t_E/3$, wherein $t_E$ is the duration of exhalation.

The duration of exhalation may be estimated as the time of pressure change from its start level at point $(t_1, P_{M1})$ until it reaches finish level at point $(t_5, P_{M5})$ (see FIG. 8). The time constant for this assumptions is $\tau_E = (t_5 - t_1)/3$, and lung compliance is:

$$C_{LT} = \frac{t_5 - t_1}{3 \cdot R_{AW}}$$

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

EXAMPLES

Example 1: Comparison of TLC Estimated by the Pulmonary Function Test Device and Plethysmograph A trial including 45 subjects, measured by the pulmonary function test device and a full body plethysmograph, was performed to compare TLC results between both methods. The trial population included 17 healthy subjects, 17 patients with COPD and 11 patients with restrictive lung disease. The trial did not provide diagnosis, as all patients participating in the trial were clinically pre-diagnosed by conventional methods prior to participation.

The terms 'plethysmograph' and 'full body plethysmograph' as used herein are interchangeable.

A statistical analysis was performed, wherein the base indicator that reflects the correlation between two variables is a linear correlation coefficient R, given by the following formula:

$$R = \frac{n \cdot \sum (S \cdot P) - (\sum S) \cdot (\sum P)}{\sqrt{n \cdot (\sum S^2) - (\sum S)^2} \cdot \sqrt{n \cdot (\sum P^2) - (\sum P)^2}}$$

where n is sample size, S indicates the data estimated by the pulmonary function test device, and P indicates the data measured by a Plethysmograph. The coefficient of determination $R^2$ denotes the strength of the linear association between two variables.

The coefficient of variation (CV) represents the ratio of the standard deviation to the mean, given by the formula:

$$CV = \frac{\sigma}{\mu}$$

where $\sigma$ is standard deviation, calculated as $\sigma = \sqrt{\Sigma(S/P)^2/(n-1)}$, and $\mu$ is the mean, calculates as $\mu = \Sigma(S/P)/n$.

Table 1 summarizes trial results of TLC estimated either by the pulmonary function test device or by a Plethysmograph. The predicted value $TLC_{PR}$ is presented in Table 1 next to the value of TLC measured by a Plethysmograph, compared to TLC estimations according to the three algorithms in accordance with some embodiments, as well as the average of the three algorithms.

Table 2 presents statistical analysis of the results presented in Table 1. The correlation coefficient of the TLC estimated by first correlated algorithm is $R_1 \approx 0.964$ and its coefficient of determination is $R_1^2 \approx 93\%$. The correlation coefficient of the TLC determined by average of two correlated algorithms (values not shown) is $R_2 \approx 0.962$ and its coefficient of determination is $R_2^2 \approx 92.6\%$, and the correlation and determination coefficient for the averaged three correlated algorithms are $R_3 \approx 0.939$ and $R_3^2 \approx 88.2\%$, respectively. The coefficient variation of the TLC estimated by the average of all three algorithms is $CV \approx 0.096$. The statistical analysis of Table 2 presents a strong correlation with the results measured by a Full Body Plethysmograph, considered to serve as a "gold standard" for such measurements.

TABLE 1

Trial results of TLC as measured by a Plethysmograph and estimated by the pulmonary function test device

| Gender, Age (Y), H (cm), W (kg) | Predicted [L] | Plethys. [L] | Pulmonary function test device [L] | | | | Pre-diagnosis |
|---|---|---|---|---|---|---|---|
| | | | Algor. #1 | Algor. #2 | Algor. #3 | Average | |
| M, 61, 175, 80 | 6.85 | 6 | 5.89 | 6.03 | 5.79 | 5.90 | Healthy |
| F, 85, 149, 70 | 4.25 | 3.85 | 3.92 | 4.28 | 4 | 4.07 | Healthy |
| M, 71, 173, 92 | 6.74 | 5.88 | 5.5 | 5.49 | 5.37 | 5.45 | Healthy |
| M, 60, 171, 75 | 6.58 | 7.81 | 8.18 | 8.56 | 7.61 | 8.12 | Healthy |
| F, 35, 165, 85 | 5.2 | 4.61 | 5.04 | 4.99 | 4.86 | 4.96 | Healthy |
| M, 89, 160, 75 | 5.7 | 5.3 | 5.06 | 5.11 | 4.9 | 5.02 | Healthy |
| M, 49, 173, 88 | 6.66 | 5.82 | 5.97 | 5.93 | 5.67 | 5.86 | Healthy |
| M, 27, 191, 69 | 8.18 | 9.31 | 9.49 | 9.03 | 9.35 | 9.29 | Healthy |
| M, 48, 179, 70 | 7.22 | 7.15 | 7.37 | 7.06 | 7.06 | 7.16 | Healthy |
| F, 86, 157, 90 | 4.57 | 3.93 | 3.6 | 3.5 | 3.63 | 3.58 | Healthy |
| M, 66, 175, 62 | 6.9 | 5.16 | 5.3 | 5.17 | 5.22 | 5.23 | Healthy |
| M, 38, 174, 77 | 6.82 | 7.1 | 7.28 | 7.14 | 7 | 7.14 | Healthy |
| F, 71, 150, 68 | 4.11 | 4.09 | 3.54 | 3.77 | 3.48 | 3.60 | Healthy |
| F, 78, 155, 90 | 3.71 | 3.82 | 3.46 | 3.72 | 3.45 | 3.54 | Healthy |
| F, 78, 147, 60 | 3.91 | 3.73 | 3.36 | 3.79 | 3.36 | 3.50 | Healthy |
| M, 58, 166, 53 | 6.18 | 5.53 | 5.33 | 5.43 | 5.23 | 5.33 | Healthy |
| M, 37, 164, 80 | 5.9 | 4.9 | 5.33 | 4.91 | 5.2 | 5.15 | Heavy Smoker |
| F, 59, 159, 80 | 4.84 | 4.78 | 4.35 | 4.2 | 4.58 | 4.38 | COPD (Chr. Asthma) |
| F, 58, 170, 100 | 5.49 | 5.6 | 5.9 | 6.03 | 5.78 | 5.90 | COPD (Asthma) |
| F, 58, 171, 61 | 5.5 | 5.72 | 5.73 | 5.69 | 6.32 | 5.91 | COPD |
| M, 70Y, 170, 68 | 6.56 | 7.43 | 7.59 | 5.34 | 6.77 | 6.57 | COPD (Emphisema) |
| F, 66Y, 166, 84 | 5.26 | 4.68 | 4.78 | 4.16 | 4.75 | 4.56 | COPD |
| M, 70, 180, 75 | 7.28 | 7.18 | 7.48 | 6.22 | 7.45 | 7.05 | COPD (Emphisema) |
| F, 70, 158, 68 | 4.8 | 4.9 | 4.22 | 3.65 | 4.45 | 4.11 | COPD (Asthma) |
| M, 73, 162, 67 | 5.86 | 4.31 | 4.87 | 4.31 | 4.75 | 4.64 | COPD |
| M, 62, 175, 97 | 6.9 | 6.11 | 5.87 | 3.19 | 6.46 | 5.17 | COPD |
| M, 74, 168, 78 | 6.34 | 5.9 | 5.88 | 4.95 | 5.91 | 5.58 | COPD |
| M, 74, 158, 71 | 5.54 | 4.49 | 4.87 | 4.53 | 5.2 | 4.87 | COPD |
| F, 86, 155, 63 | 4.44 | 3.43 | 3.27 | 2.57 | 3.39 | 3.08 | COPD (Asthma) |
| M, 92, 164, 76 | 6.02 | 4.79 | 5.19 | 3.46 | 5.38 | 4.68 | COPD (Asthma) |
| F, 63, 155, 89 | 4.44 | 2.81 | 3.39 | 2.5 | 3.5 | 3.13 | COPD |
| M, 68Y, 174, 75 | 6.82 | 6.2 | 5.78 | 4.91 | 6.84 | 5.84 | COPD |
| M, 80, 163, 86 | 5.94 | 4.29 | 4.79 | 4.1 | 5 | 4.63 | COPD |
| M, 65, 165, 100 | 6.06 | 6.6 | 6.03 | 5.75 | 6.18 | 5.99 | COPD (Asthma) |
| F, 75, 149, 66 | 4.25 | 2.25 | 1.82 | 1.6 | 1.91 | 1.78 | Restrictive (Fibrosis) |
| M, 79, 163, 66 | 5.94 | 3.28 | 4 | 2.71 | 4.1 | 3.60 | Restrictive (Fibrosis) |
| M, 43, 176, 128 | 6.98 | 4.75 | 4.96 | 3.96 | 4.9 | 4.61 | Restrictive |

TABLE 1-continued

Trial results of TLC as measured by a Plethysmograph and estimated by the pulmonary function test device

| Gender, Age (Y), H (cm), W (kg) | Predicted [L] | Plethys. [L] | Pulmonary function test device [L] | | | | Pre-diagnosis |
|---|---|---|---|---|---|---|---|
| | | | Algor. #1 | Algor. #2 | Algor. #3 | Average | |
| M, 64, 167, 117 | 6.26 | 2.76 | 3.44 | 2.37 | 3.66 | 3.16 | Restrictive |
| M, 5, 177, 88 | 7.06 | 5.73 | 5.88 | 5.26 | 5.86 | 5.67 | Restrictive |
| M, 69, 168, 85 | 6.34 | 3.92 | 4.3 | 4.03 | 4.81 | 4.38 | Restrictive |
| F, 65, 154, 82 | 4.37 | 3.18 | 3.32 | 2.84 | 3.34 | 3.17 | Restrictive |
| F, 54, 161, 101 | 4.84 | 3.33 | 3.52 | 3.38 | 3.54 | 3.48 | Restrictive |
| M, 77, 175, 94 | 6.9 | 3.45 | 3.94 | 3.26 | 4.05 | 3.75 | Rest. + Light COPD |
| M, 70, 167, 86 | 6.26 | 3.85 | 4.52 | 3.93 | 4.63 | 4.36 | Rest. + Light COPD |
| M, 73, 164, 89 | 6.01 | 4.1 | 4.5 | 4.2 | 4.5 | 4.40 | Restrictive (Fibrosis) |

* M denotes Male, F denotes Female, H denotes Height, W denotes Weight, 'Plethys.' denotes results of plethysmography measurements, 'Algor.' denotes Algorithm, 'Average' refers to average of algorithms #1-#3.

TABLE 2

Trial statistical analysis results

| | Algorithm #1 | Average of Alg. #1 & #2 | Average of Alg. #1, #2 & #3 |
|---|---|---|---|
| Correlation Coefficient R | 0.964 | 0.962 | 0.939 |
| Coefficient of Determination $R^2$ | 0.930 | 0.926 | 0.882 |
| Coefficient of Variation CV | 0.085 | 0.092 | 0.096 |

Figure 10:
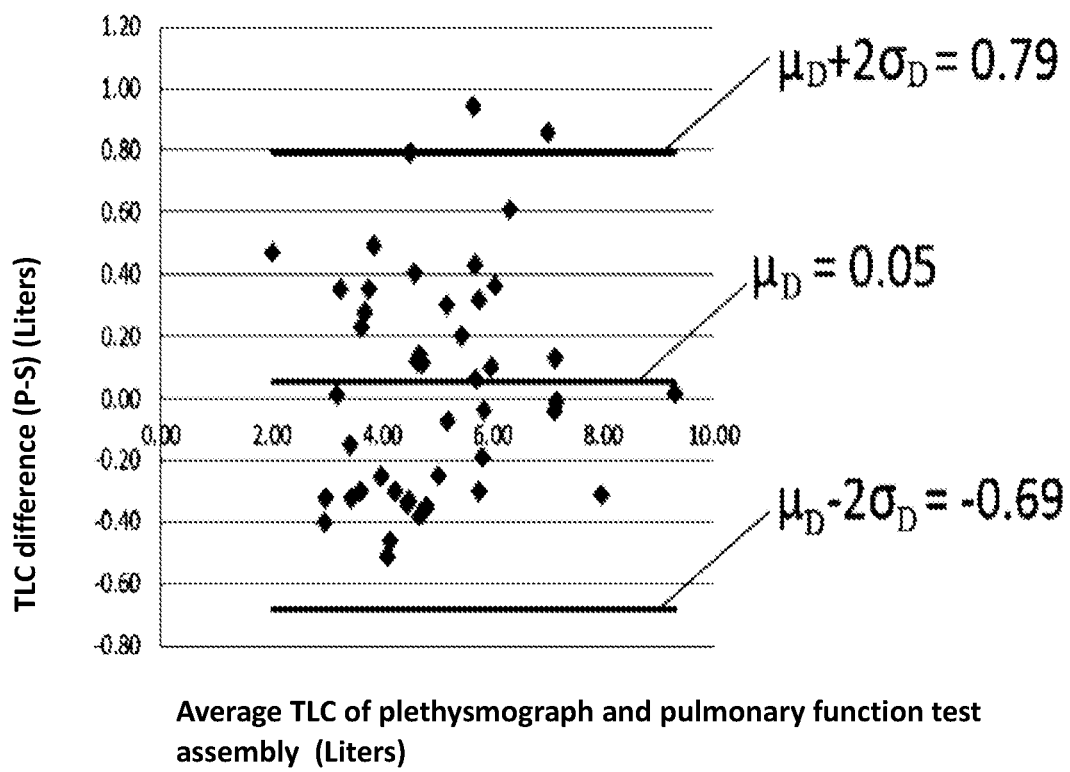
FIG. 10 shows an example of a Bland-Altman plot of Total Lung Capacity values measured by a plethysmograph and a pulmonary function test device.

FIG. 10 shows a Bland-Altman plot of the difference between TLC values measured by Plethysmograph and the pulmonary function test device against their mean. Such a plot is considered to be more informative than the correlation coefficient R in determining how close the two methods of measurement are. The Bland-Altman method calculates the mean difference between two methods of measurement (the "bias"), and 95% limits of agreement as the mean difference ($2\sigma$, or more precisely $1.96\sigma$). It is expected that the 95% limits include 95% of the differences between the two measurement methods. The plot in FIG. 10 is a presentation of the 95% limits of agreement, mainly intended for visual estimation of how well two methods of measurement agree. The smaller the range between these two limits the better the agreement is. Such a plot also provides an assessment of the possible relationship between the measurement error and the true value. In this case, the mean difference is defined as $\mu_D = \Sigma(P-S)/n$, and the standard deviation of the difference is $\sigma_D = \sqrt{\Sigma(P-S)^2/(n-1)}$. For the TLC data of the current trial, the mean difference is $\mu_D = 0.05$ l and standard deviation of the difference is $\sigma_D = 0.37$ l. If the differences are normally distributed (Gaussian distribution), 95% of the differences will be included between $\mu_D - 2 \cdot \sigma_D$ and $\mu_D + 2 \cdot \sigma_D$, or more precisely, between $\mu_D - 1.96 \cdot \sigma_D$ and $\mu_D + 1.96 \cdot \sigma_D$. Assuming that the differences included within $\mu_D \pm 2 \cdot \sigma_D$ would not be clinically important, they may be referred to as the "limits of agreement". For TLC data of the current trial, said limits of agreement are:

$$\mu_D - 2 \cdot \sigma_D = 0.05 - 2 \cdot 0.37 = -0.69 \text{ l}$$

$$\mu_D + 2 \cdot \sigma_D = 0.05 + 2 \cdot 0.37 = 0.79 \text{ l}$$

Thus, TLC estimations based on measurements of by the pulmonary function test device may be 0.69 l below or 0.79 l above Plethysmograph measurements. Such values are known in the art to be acceptable for clinical purposes, as reported, for example, in R. M. Schwartzstein, and M. J. Parker, Respiratory Physiology: A Clinical Approach (integrated Physiology), (Lippincott Williams & Wilkins, 2005), which noted that the clinically acceptable range in the comparison of lung volume measurement between body plethysmography and helium dilution is ±0.9 liter Example 2: Repeatability Assessment A trial involving two subjects was performed in order to test repeatability, which is defined by the ISO as the closeness of agreement between independent test results under repeatability conditions that are as constant as possible, where independent test results are obtained with the same methods, on identical test items, in the same laboratory, performed by the same operator, using the same equipment, within short intervals of time. The first subject was a healthy 62 years old male, and the second subject was a 60 years old female suffering from chronical asthma disease. The Coefficient of Repeatability (CR) can be calculated as 1.96 times the standard deviation of the differences between Plethysmograph (P) and pulmonary function test device (S) data:

$$CR = 1.96 \cdot \sqrt{\frac{\Sigma(P-S)^2}{m}}$$

where 'm' is the number of observations for each subject. As known in the art, for example in S. A. McKenzie et al, Arch. Dis. Child; 87: pp. 248-251 (2002), the CR is the value below which the absolute differences between the two measurements, Full Body Plethysmograph and pulmonary function test device, would lie with 0.95 probabilities.

Figure 11A:
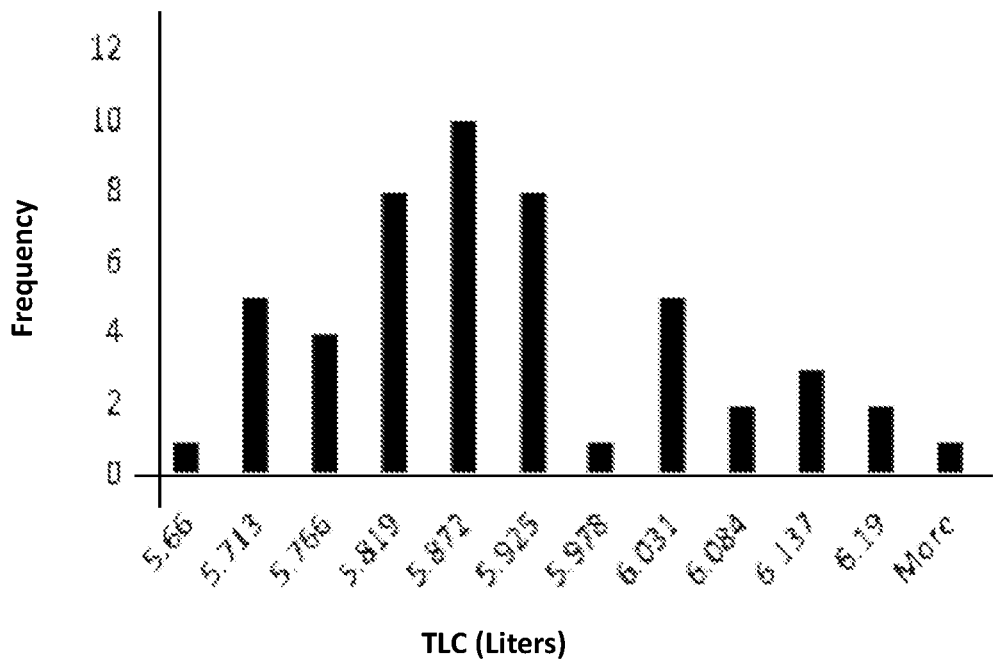
FIG. 11a shows a Total Lung Capacity histogram measured for a healthy subject, during a repeatability trial.
Figure 11B:
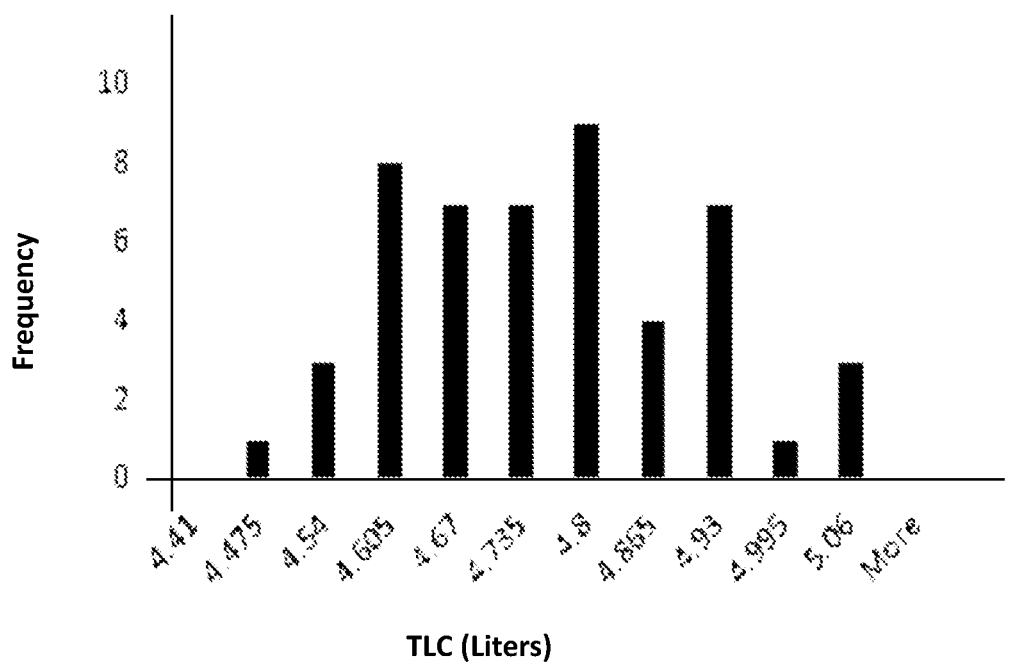
FIG. 11b shows a Total Lung Capacity histogram measured for a patient suffering from chronical asthma disease, during a repeatability trial.

FIG. 11a shows trial results histogram for the first subject, and FIG. 11b shows trial results histogram for the second subject, wherein bins are of The number of observations was set to 50 for each subject.

Table 3 shows the results of the repeatability tests of both subjects, which may be interpreted as acceptable for medical practice.

TABLE 3

Repeatability test results

| Parameters | Healthy subject (Plethysm. TLC = 6.0 L) | Chronic Asthma patient (Plethysm. TLC = 4.78 L) |
|---|---|---|
| Maximum (L) | 6.19 | 5.05 |
| Minimum (L) | 5.66 | 4.42 |

TABLE 3-continued

Repeatability test results

| Parameters | Healthy subject (Plethysm. TLC = 6.0 L) | Chronic Asthma patient (Plethysm. TLC = 4.78 L) |
|---|---|---|
| Average (L) | 5.88 | 4.73 |
| CR (L) | 0.356 | 0.302 |

Example 3: Airway Resistance Estimation

A pre-clinical trial was performed on 10 voluntary patients. Estimation of the airway resistance, which is the ratio between pressure and flow, was performed for the pulmonary function test device and a plethysmograph model ZAN 500, referred to as the gold standard.

Table 4 shows the results of the airway resistance assessment for both the pulmonary function test device and the plethysmograph. The results indicate that there is a good correlation between resistance estimates of both systems for all 10 subjects. The differences in the results between the plethysmograph and the pulmonary function test device may be attributed to two major reasons: one important difference between said device and the plethysmograph is that said device estimates the bronchial airway resistance value, while the plethysmograph enables measurement of the total airway resistance, and another difference between the two systems is that for said device, the resistance is calculated around the pressure $P_M=P_{M3}$ (see FIG. 8), and in the plethysmograph said resistance is measured at the time when flow rate in the range of 0.5-1 L/s.

Example 4: Lung Compliance Estimation

A pre-clinical trials were performed on 10 voluntary patients, measured by the pulmonary function test, was performed to validate method of lung compliance estimation. Table 5 shows estimation results, corresponding to lung compliance at point $(t_3, P_{M3})$.

TABLE 4

Airway resistant assessment

| Subject's Gender & Age | Plethysmograph (kPa · s)/l | pulmonary function test device (kPa · s)/l |
|---|---|---|
| Male, 61 years | 0.568 | 0.506 |
| Male, 71 years | 0.403 | 0.489 |
| Male, 47 years | 0.805 | 0.686 |
| Female, 59 years | 0.795 | 0.746 |
| Female, 85 years | 0.498 | 0.541 |
| Male, 37 years | 0.739 | 0.732 |
| Female, 35 years | 0.307 | 0.520 |

TABLE 4-continued

Airway resistant assessment

| Subject's Gender & Age | Plethysmograph (kPa · s)/l | pulmonary function test device (kPa · s)/l |
|---|---|---|
| Male, 89 years | 0.545 | 0.705 |
| Female, 85 years | 0.543 | 0.490 |
| Male, 59 years | 0.605 | 0.758 |

TABLE 5

Lung compliance

| Subject's Gender & Age | Lung Compliance ($[m^3/Pa] \times 10^{-6}$) |
|---|---|
| Male, 61 years | 1.153 |
| Male, 71 years | 1.48 |
| Male, 47 years | 1.413 |
| Female, 59 years (Chron. Asthma) | 0.936 |
| Female, 85 years | 0.962 |
| Male, 37 years | 1.387 |
| Female, 35 years | 1.168 |
| Male, 89 years | 2.108 |
| Female, 85 years | 1.544 |
| Male, 59 years | 1.493 |

Example 5: Diagnosis of Lung Diseases

The main clinical objectives of respiratory function measurements include diagnosis, severity assessment, treatment monitoring and evaluation of prognosis. Spirometry serves as a useful diagnostic device, which measures, amongst other parameters, vital capacity (VC) and force expiratory volume in 1 second (FEV1). These parameters permit differentiation between restrictive and obstructive respiratory diseases. Spirogram flow-volume curves are used for diagnosis. However, combined obstructive and restrictive diseases are not always distinguished as single ailments inform such curves.

An objective, in accordance with some embodiments, of the pulmonary function test device's time-pressure curves and diagnostic indices, such as TI, VI, PI and $TVI_O$, is to provide a tool for lung disease diagnosis.

Figure 12A:
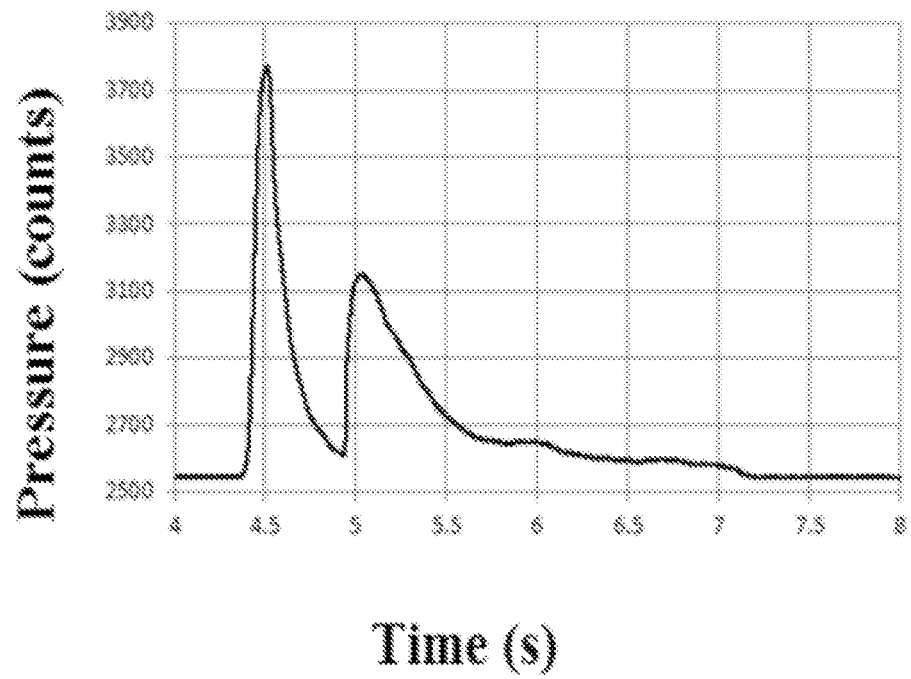
FIG. 12a shows an example of the graph of gauge pressure reading over time during a sequential forced exhalation event, measured for healthy patients, in accordance with some embodiments.
Figure 12B:
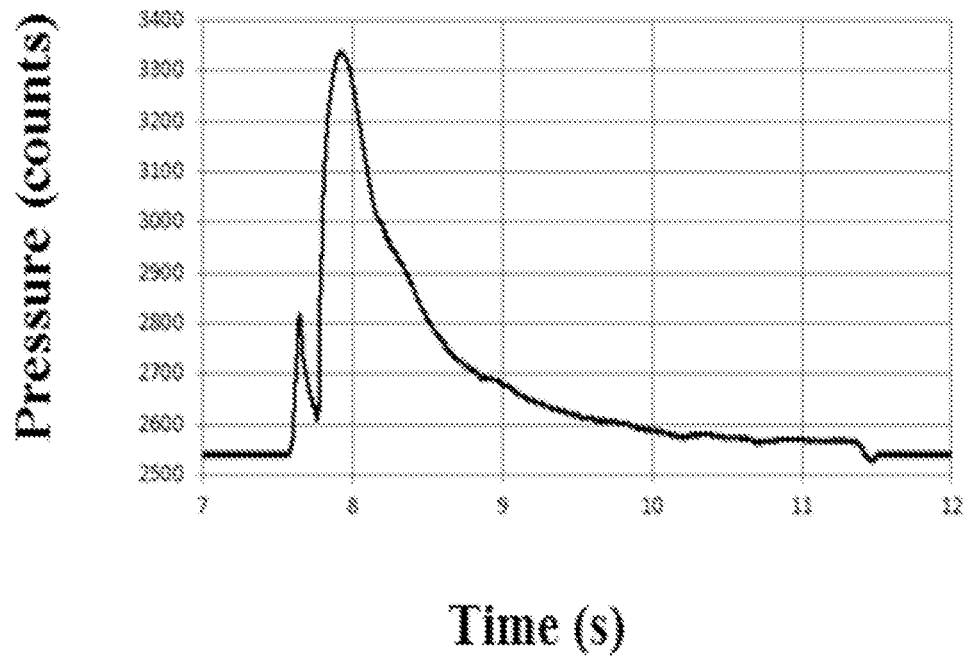
FIG. 12b depicts an example of the graph of gauge pressure reading over time during a sequential forced exhalation event, measured for patients suffering from an obstructive lung disease, in accordance with some embodiments.
Figure 12C:
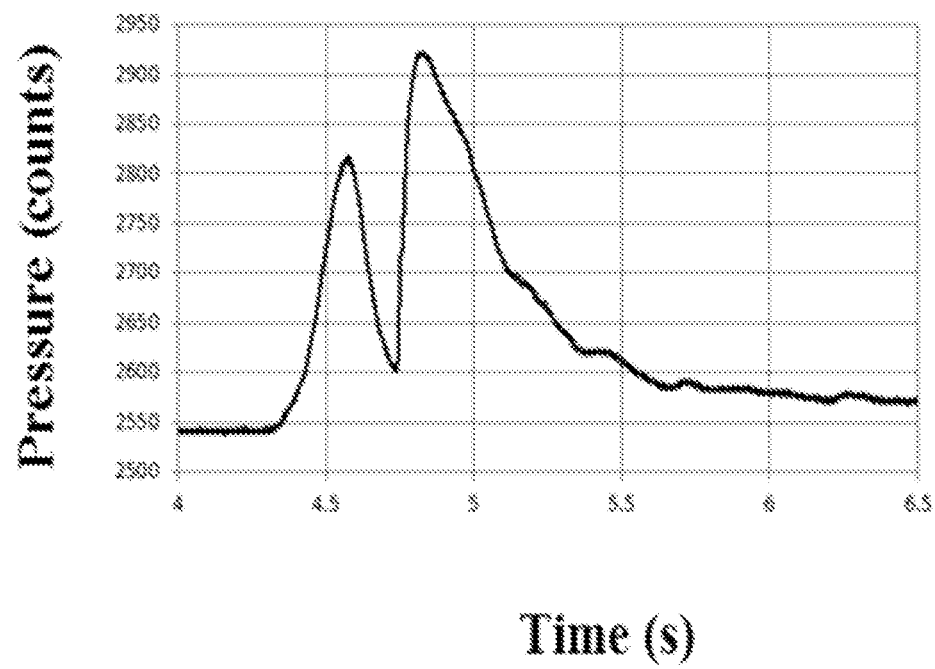
FIG. 12c depicts an example of the graph of gauge pressure reading over time during a sequential forced exhalation event, measured for patients suffering from a restrictive lung disease, in accordance with some embodiments.

FIG. 12a-c shows typical patterns of the pulmonary function test device's time-pressure curves differences between healthy (FIG. 12a), restrictive (FIG. 12b) and obstructive (FIG. 12c) subjects, in accordance with some embodiments.

Table 6 shows different value ranges of the diagnostic indices, in accordance with some embodiments, that may allow discrimination between different types of lung diseases.

TABLE 6

Diagnostic indices for different conditions

| Subject Condition | Time Index TI | Volume Index VI | Pressure Index PI | Obstructive Index $TVI_O$ |
|---|---|---|---|---|
| Healthy | $0.5 < TI \le 0.8$ | $0.4 < VI \le 0.8$ | $0.3 < PI \le 0.8$ | $TVI_O < 2.0$ |
| Obstructive | $0.8 < TI \le 1.2$ | $1.5 < VI \le 4.5$ | $1.4 < PI \le 4.0$ | $2.0 \le TVI_O \le 4.0$ |
| Restrictive | $0.3 < TI \le 0.5$ | $0.8 < VI \le 1.5$ | $0.8 < PI \le 1.4$ | $TVI_O < 2.0$ |

A trial involving 12 subjects, including healthy subjects, as well as patients suffering from either obstructive or restrictive lung disease, was performed to assess the pulmonary function test device's diagnostic capabilities.

Table 7 shows the resulting indices and their interpretation for the pulmonary function test device's measurements, compared to results of traditional diagnostics. Results show that there is a good correlation between the diagnostic results of the pulmonary function test device and traditional diagnostics. Nevertheless, further statistical analysis of curve patterns and index values for a wider variety of lung diseases of larger patient population may provide more reliable and accurate diagnostic capabilities as interpreted for measurements made by the pulmonary function test device.

TABLE 7

Diagnostic results of the pulmonary function test device

| Subject's Gender & Age | Time Index TI | Volume Index VI | Pressure Index PI | Obstructive Index $TVI_O$ | Traditional Diagnostic | STS Diagnostic |
|---|---|---|---|---|---|---|
| Male, 61 years | 0.655 | 0.671 | 0.507 | 1.02 | Healthy | Healthy |
| Male, 71 years | 0.552 | 0.44 | 0.3 | 0.82 | Healthy | Healthy |
| Male, 47 years | 0.512 | 0.405 | 0.312 | 0.77 | Healthy | Healthy |
| Female, 35 years | 0.585 | 0.612 | 0.796 | 0.937 | Healthy | Healthy |
| Female, 59 years | 0.824 | 2.81 | 2.87 | 2.37 | Chr. Asthma | Obstruct. |
| Mail, 70 years | 0.855 | 3.31 | 1.4 | 2.51 | Emphysema | Obstruct. |
| Female, 58 years | 0.835 | 2.91 | 3.27 | 2.3 | COPD | Obstruct. |
| Female, 70 years | 0.896 | 4.41 | 1.75 | 3.11 | Asthma | Obstruct. |
| Female, 75 years | 0.392 | 1.0 | 0.662 | 0.99 | Fibrosis | Restrict. |
| Female, 54 years | 0.548 | 0.81 | 1.17 | 1.0 | Restrict. | Restrict. |
| Mail, 79 years | 0.548 | 1.58 | 1.25 | 1.4 | Fibrosis | Restrict. |
| Female, 65 years | 0.502 | 1.05 | 0.88 | 1.09 | Restrict. | Restrict. |

Although the invention is described in conjunction with specific embodiments thereof, it is evident that numerous alternatives, modifications and variations that are apparent to those skilled in the art may exist. It is to be understood that the invention is not necessarily limited in its application to the details of construction and the arrangement of the components and/or methods set forth herein. Other embodiments may be practiced, and an embodiment may be carried out in various ways. Accordingly, the invention embraces all such alternatives, modifications and variations that fall within the scope of the appended claims.

The invention claimed is:

1. A device for determining at least one pulmonary function characteristic, the device comprising
   (i) at least one chamber comprising
       at least one gas inlet port, configured to receive gas flow;
       a distal element comprising at least one distal opening;
       at least one pressure transducer configured to detect pressure within the at least one chamber and to produce a signal upon detecting pressure at about a predetermined threshold;
   (ii) at least one shutter module connected to said distal element, said at least one shutter module comprising at least one shutter opening; and
   (iii) an actuator configured to displace, or induce displacement, of the at least one shutter module upon receiving the signal, or a signal derived from said signal,
   wherein the at least one shutter opening is configured to allow passage of gas flow from the at least one distal opening to the atmosphere through a first total effective area enclosed by a perimeter of the at least one shutter opening, when the shutter module is in a state of first end position; and
   wherein upon said displacement the first total effective area changes to a second total effective area, when the shutter module is in second end position.

2. The device of claim 1, wherein the chamber further comprises a laminar flow diffuser.

3. The device of claim 2, wherein the at least one pressure transducer is configured to detect pressure within the space between the laminar flow diffuser and the distal element.

4. The device of claim 1, further comprising a mouthpiece connected to the at least one gas inlet port, and configured to enable delivery of exhaled gas flow to the at least one gas inlet port.

5. The device of claim 4, wherein the mouthpiece further comprises an anti-bacteriological filter.

6. The device of claim 1, further comprising a handle connected to the at least one chamber.

7. The device of claim 1, wherein the actuator is a rotary actuator and the shutter module is a shutter wheel having a circular form, and wherein the actuator is configured to displace, or to induce displacement of, the at least one shutter wheel by rotation.

8. The device of claim 7, further comprising a shutter pin and a hard stop comprising a groove, wherein the shutter pin is located within the groove, and wherein the shutter pin is configured to limit the range of displacement of the shutter module.

9. The device of claim 7, wherein the shutter wheel comprises at least one shutter opening, wherein the at least one shutter opening allows passage of gas flow from the at least one distal opening through the area enclosed by the perimeter of the at least one shutter opening, or through any portion thereof.

10. The device of claim 7, wherein said shutter wheel and said distal element are detached from one another allowing passage of gas flow from the at least one distal opening through an area extending between the circumference of said shutter wheel and said distal element.

11. The device of claim 7, wherein the shutter wheel comprises at least one shutter edge opening, wherein the at least one shutter edge opening allows passage of gas flow from the at least one distal opening through the area enclosed by the perimeter of the at least one shutter edge opening, or through any portion thereof.

12. The device of claim 1, further comprising a control module, wherein the control module is configured to receive one or more signals from the at least one pressure transducer.

13. The device of claim 12, wherein the control module is configured to provide the one or more signals to the actuator.

14. The device of claim 13, wherein the control module is configured to transmit the one or more signals to the external device in real time.

15. The device of claim 12, wherein the control module is configured to transmit the one or more signals to an external device.

16. The device of claim 12, wherein the control module is configured to store the one or more signals.

17. A method for evaluating at least one pulmonary function characteristic in a subject in need thereof, comprising the steps of:
(i) providing the device of claim 1;
(ii) receiving gas exhalation from a subject in need thereof, through the gas inlet port;
(iii) detecting pressure within the at least one chamber;
(iv) producing pressure versus time curve and identifying a first peak pressure;
(v) toggling the shutter module if the detected pressure post the first peak pressure is within the range of a predetermined pressure threshold;
(vi) identifying a second peak pressure and an end point pressure in the pressure versus time curve; and
(vii) deriving from said pressure versus time curve at least one value related to at least one pulmonary function characteristics of said subject in need thereof.

18. The method of claim 17, further comprising the step of identifying on the curve of step (vi) a pressure volume indicator point, wherein the pressure volume indicator point post the second peak pressure is a pressure within the range of a predetermined pressure threshold.

19. The method of claim 18, further comprising the step of determining an airway resistance based on the predetermined pressure threshold and the second peak pressure.

20. The method of claim 19, further comprising the step of determining a lung compliance based on the airway resistance and the end point pressure.

21. The method of claim 18, further comprising determining a group of volume related indices; and producing a diagnostic event based on the group of volume related indices.

22. The method of claim 17 wherein said at least one value comprises any one or more of Thoracic Gas Volume (TGV) and Total Lung Capacity (TLC), and wherein the derivative of said pressure versus time curve includes at least one linear portion.

23. The method of claim 22, further comprising identifying on the curve of step (vi) a pressure volume indicator point, wherein the at least one linear portion is the derivative of the pressure during a time period encompassing the pressure volume indicator point.

24. The method of claim 17, wherein said at least one value comprises any one or more of TGV and TLC, and wherein said pressure versus time curve includes at least one exponential portion.

25. The method of claim 24, wherein the at least one exponential portion is during a time period extended between the second peak pressure and the end point pressure.

26. The method of claim 17, wherein said at least one value comprises any one or more of TGV and TLC, and wherein said pressure versus time curve includes at least one parabolic portion.

27. The method of claim 26, wherein the at least one parabolic portion is the pressure during a time period extended between the second peak pressure and the end point pressure.

* * * * *